United States Patent
Butuc

(12) 
(10) Patent No.: US 6,881,776 B2
(45) Date of Patent: Apr. 19, 2005

(54) GEL COMPOSITIONS

(75) Inventor: S. Gina Butuc, The Woodlands, TX (US)

(73) Assignee: Penreco, Houston, TX (US)

(*) Notice: Subject to any disclaimer, the term of this patent is extended or adjusted under 35 U.S.C. 154(b) by 354 days.

(21) Appl. No.: 09/853,552

(22) Filed: May 11, 2001

(65) Prior Publication Data

US 2002/0055562 A1 May 9, 2002

Related U.S. Application Data

(63) Continuation-in-part of application No. 09/419,571, filed on Oct. 18, 1999.
(60) Provisional application No. 60/106,094, filed on Oct. 29, 1998.

(51) Int. Cl.$^7$ .............................. C08L 53/00; C08K 5/10
(52) U.S. Cl. ..................... 524/284; 524/379; 524/366; 524/388; 524/505
(58) Field of Search ................................ 524/505, 284, 524/379, 366, 388

(56) References Cited

U.S. PATENT DOCUMENTS

| | | |
|---|---|---|
| 3,645,705 A | 2/1972 | Miller et al. |
| 3,819,342 A | 6/1974 | Gunderman et al. |
| 4,540,510 A | 9/1985 | Karl |
| 5,132,355 A | 7/1992 | Nahlovsky |
| 5,221,534 A | 6/1993 | DesLauriers et al. |
| 5,412,022 A | 5/1995 | Andres et al. |
| 5,508,334 A | 4/1996 | Chen |
| 5,558,872 A | 9/1996 | Jones et al. |
| 5,578,089 A | 11/1996 | Elsamaloty |
| 5,756,082 A | 5/1998 | Cashin et al. |
| 5,843,194 A | 12/1998 | Spaulding |
| 5,879,694 A | 3/1999 | Morrison et al. |
| 6,433,068 B1 * | 8/2002 | Morrison et al. ........... 524/505 |

FOREIGN PATENT DOCUMENTS

| | | |
|---|---|---|
| EP | 0210655 | 2/1987 |
| EP | 0147146 | 4/1991 |
| EP | 0497144 B1 | 1/1992 |
| EP | 0898958 A1 | 7/1998 |
| EP | 0898960 A1 | 8/1998 |
| WO | WO 91/05014 | 4/1991 |
| WO | WO98/17243 | 4/1998 |
| WO | WO98/42298 | 10/1998 |
| WO | WO99/27042 | 6/1999 |

OTHER PUBLICATIONS

PCT Search Report, Feb. 24, 2000.
Tashenbuch der Kunststoff–Additive, R. Gachter et al., Haner Verlag, Munchen. Pp. 427–428, 1989.
PCT Written Opinion, Aug. 25, 2000.
International Preliminary Examination Report, Jan. 24, 2001.

* cited by examiner

Primary Examiner—Peter D. Mulcahy
(74) Attorney, Agent, or Firm—Jenkens & Gilchrist, A Professional Corporation

(57) ABSTRACT

Two-phase gel compositions are provided. The two-phase gel compositions are obtained by mixing a gelled ester composition comprising a mixture of an ester compound and a polymer compound selected from the group consisting of triblock copolymers, star polymers, radial polymers, multi-block copolymers, and a combination thereof and a hydrophobic, non polar solvent. The gelled ester composition has a viscosity $\eta_1$ and the solvent has a viscosity $\eta_2$. The two-phase gel composition is substantially free of phosphate compounds and has a viscosity $\eta$ which is greater than or equal to $\eta_1$ and which is greater than or equal to $\eta_2$. The two-phase gel compositions are also obtained by mixing a gelled ether composition, a gelled alcohol composition, a gelled naturally-occurring fat and oil composition or a combination thereof with a hydrophobic, non polar solvent. The two-phase gel compositions may be used to suspend various solids, liquids and/or gases.

49 Claims, 3 Drawing Sheets

GEL COMPOSITIONS

CROSS-REFERENCE TO RELATED APPLICATIONS

This patent application is a continuation-in-part of U.S. application Ser. No. 09/419,571, filed Oct. 18, 1999, entitled "Gel Compositions" which claims priority to a previously filed U.S. provisional application Ser. No. 60/106,094, filed Oct. 29, 1998, entitled "Gel Composition," in the name of Lin Lu, Jack Cunningham, Jr., and David S. Morrison. The disclosures of the aforementioned applications are incorporated by reference in their entirety herein.

FIELD OF THE INVENTION

This invention relates to gel compositions which are combinations of a gelled ester composition, a gelled ether composition, a gelled alcohol composition, a gelled naturally-occurring fat and oil composition, or a combination thereof with a solvent and methods of increasing the viscosity of gelled ester compositions, gelled ether compositions, gelled alcohol compositions, and gelled naturally-occurring fat and oil compositions.

BACKGROUND OF THE INVENTION

Numerous gel compositions are known in the art. Gel compositions have proven to be useful in a wide variety of applications, such as in cosmetic, health and beauty, home care, and industrial applications.

Gel compositions have been used in a variety of cosmetic and health and beauty applications. Some gel compositions have proven to be convenient and efficient vehicles or carriers for the application of various active ingredients to the skin. Such active ingredients include sunscreens, antiperspirants, deodorants, perfumes, cosmetics, emollients, insect repellants, medicaments, and the like. Cosmetic and health and beauty products incorporating a gel composition and those made entirely from a gel composition may be in the form of a liquid, soft gel, semi-solid, or solid. Rubbing a liquid, soft gel, semi-solid, or solid containing an effective amount of an active ingredient dissolved or dispersed therein against the skin causes transfer of the gel composition to the skin surface in a layer form, leaving the active ingredient within the layer on the desired skin surface.

For cosmetic and health and beauty applications, a gel composition preferably should have one or more of the following desired properties: transparency, compatibility with an active ingredient, controlled release of an active ingredient, minimization of skin irritation, and the ability to suspend organic and inorganic materials such as colored pigments, glitters, water, air, metal oxides, sunscreen active particulates, and fragrances. For example, in sunscreen applications, it is desirable if the gel itself can act as a sunscreen active ingredient while in a cosmetic application, it is desirable if the gel can provide suspension and controlled release properties. Moreover, a gel composition used in cosmetic and health and beauty applications should moisturize the skin and exhibit water wash-off resistance but should not have significant syneresis.

Gel compositions have also been used in a variety of home care applications. For home care applications, a gel composition should preferably offer one or one or more of the following desired properties: transparency, compatibility with an active ingredient, controlled release of an active ingredient, and the ability to suspend organic and inorganic materials, such as colored pigments, glitters, water, air, metal oxides, fragrances, and the like. For example, in air freshener applications, the properties that are important are controlled release and viscosity.

In addition, gel compositions have been used in a variety of industrial applications. For industrial applications, a gel composition should preferably offer one or one or more of the following desired properties: suspension, moisture barrier, rheology, control of rheology, solvency, controlled release of an active or volatile ingredient, wetting, self-emulsifying, transparency, compatibility with an active ingredient, and the like. For example, in the paint industry, the properties that are important are suspension and controlled release while the properties that are important are suspension and the control of rheology with explosive emulsions.

A gel composition is typically made by mixing one or more compounds to be gelled with a gelling agent. When a gel composition is then combined with or loaded with a relatively low viscosity solvent, it is expected that the resulting gel composition will have a viscosity which is lower than the viscosity of the original gel composition. However, in many cosmetic, health and beauty, home care, and industrial applications, it may be desirable to load or combine a gel composition with a solvent to produce a resulting gel composition having an increased viscosity.

For example, in drilling applications, oil needs to be suspended and pumped to the surface. It is desirable to be able to increase the viscosity of gel compositions used in a drilling application because a gel composition with a low viscosity may not be able to suspend the oil. Also, in explosive emulsion applications, it is desirable to be able to increase the viscosity of gel compositions used in the explosive emulsion because a gel composition with a low viscosity may not be able to hold in the gas and avoid detonation. Also by way of example, in the drilling, formation, and treatment of subterranean formations such as wells, it is often desirable or necessary that the gel compositions have a relatively low initial viscosity and an increased viscosity once placed in the well bore or subterranean formation to be treated.

Hence, there exists a need for exploring methods of increasing the viscosity of gel compositions when combined with low viscosity solvents. Gel compositions, containing esters, ethers, alcohols, and vegetable oils are less common than gelled mineral oils or gelled hydrocarbons. Hence, there also exists a need for exploring methods of increasing the viscosity of gelled ester, gelled ether, gelled alcohol, and gelled naturally-occurring fat and oil compositions.

SUMMARY OF THE INVENTION

The invention meets the aforementioned need in one or more of the following aspects. In one aspect, the invention relates to a gel composition referred to herein as a two-phase gel composition. The two-phase gel composition is a combination of at least two components. The first component is a gelled ester composition, a gelled ether composition, a gelled alcohol composition, a gelled naturally-occurring fat and oil composition, or a combination thereof. The second component is a hydrophobic, non-polar solvent. The two-phase gel composition resulting from the mixture of the first and second components has a viscosity which is greater than or equal to the viscosity of the individual components used to make the two-phase gel composition either alone or in combination.

In some embodiments, the two-phase gel composition maybe substantially free of phosphate compounds, although one or more of these compounds may be present in other embodiments. Similarly, some two-phase gel compositions may be substantially free of any antioxidants, while other two-phase gel compositions may include one or more antioxidants.

In some embodiments of the invention, the two-phase gel composition may optionally include additional components. In some embodiments, the additional component may be a suspended component. In other embodiments, the additional component maybe an active ingredient.

In another aspect, the invention relates to a method of increasing the viscosity of a gel composition. The method includes (a) mixing a gelled ester composition, a gelled ether composition, a gelled alcohol composition, a gelled naturally-occurring fat and oil composition, or a combination thereof with one or more hydrophobic, non-polar solvents to form a mixture; (b) heating the mixture; (c) agitating the mixture until the mixture becomes homogeneous; and (d) cooling the mixture to form a two-phase gel composition. The resulting two-phase gel composition has a viscosity which is greater than or equal to the viscosity of the individual components used to make the two-phase gel composition either alone or in combination.

In still another aspect, the invention relates to a method of increasing the viscosity of a gel composition. The method includes (a) heating a gelled ester composition, a gelled ether composition, a gelled alcohol composition, a gelled naturally-occurring fat and oil composition, or a combination thereof; (b) mixing the heated gel composition with one or more hydrophobic, non-polar solvents to form a mixture; (c) agitating the mixture until the mixture becomes homogeneous; and (d) cooling the mixture to form a two-phase gel composition. The resulting two-phase gel composition has a viscosity which is greater than or equal to the viscosity of the individual components used to make the two-phase gel composition either alone or in combination.

In yet another aspect, the invention relates to a method of increasing the viscosity of a gel composition. The method includes (a) heating one or more hydrophobic, non-polar solvents; (b) mixing the heated solvent with a gelled ester composition, a gelled ether composition, a gelled alcohol composition, a gelled naturally-occurring fat and oil composition, or a combination thereof to form a mixture; (c) agitating the mixture until the mixture becomes homogeneous; and (d) cooling the mixture to form a two-phase gel composition. The resulting two-phase gel composition has a viscosity which is greater than or equal to the viscosity of the individual components used to make the two-phase gel composition either alone or in combination.

In another aspect, the invention relates to a method of increasing the, viscosity of a gel composition. The method includes (a) heating one or more hydrophobic, non-polar solvents; (b) separately heating a gelled ester composition, a gelled ether composition, a gelled alcohol composition, a gelled naturally-occurring fat and oil composition, or a combination thereof; (c) mixing the heated solvent with the heated gel composition to form a mixture; (d) agitating the mixture until the mixture becomes homogeneous; and (e) cooling the mixture to form a two-phase gel composition. The resulting two-phase gel composition has a viscosity which is greater than or equal to the viscosity of the individual components used to make the two-phase gel composition either alone or in combination.

In yet another aspect, the invention relates to a method of increasing the viscosity of a gel composition. The method includes mixing a gelled ester composition, a gelled ether composition, a gelled alcohol composition, a gelled naturally-occurring fat and oil composition, or a combination thereof with a hydrophobic, non-polar solvent to form a two-phase gel composition. The resulting two-phase gel composition has a viscosity which is greater than or equal to the viscosity of the individual components used to make the two-phase gel composition either alone or in combination.

Properties and advantages of the embodiments of the invention become apparent with the following description.

DESCRIPTION OF EMBODIMENTS OF THE INVENTION

Figure 1:
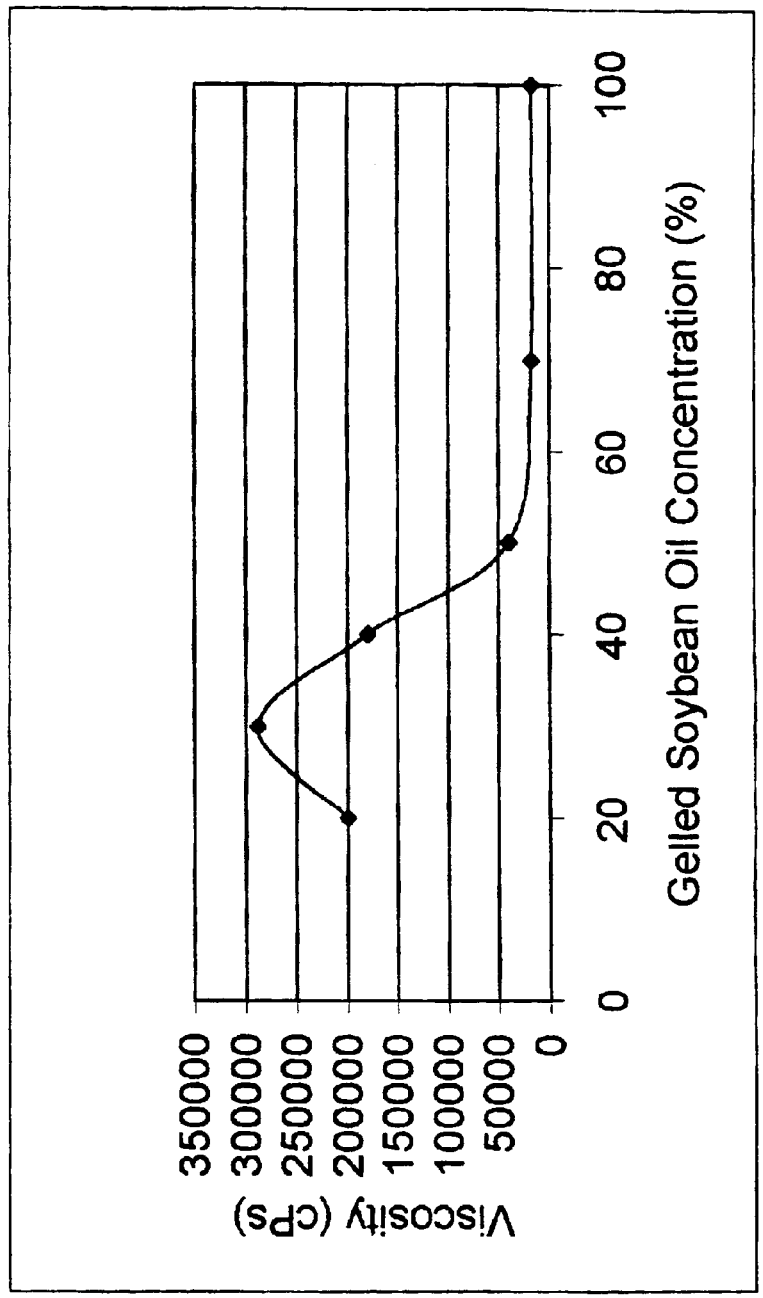
FIG. 1 is a graph of viscosity versus concentration for a two-phase gel composition according to one embodiment of the invention.

Embodiments of the invention are, in part, based on the discovery that a gelled composition with a relatively low viscosity can be combined with or loaded with a relatively low viscosity solvent to achieve a gel composition referred to herein as a two-phase gel composition having a viscosity which is greater than or equal to the viscosity of the individual components used to make the two-phase gel composition either alone or in combination. The two-phase gel composition is a combination of at least two components. The first component is a gelled ester composition, a gelled ether composition, a gelled alcohol composition, a gelled naturally-occurring fat and oil composition, or a combination thereof. The second component is a relatively non-polar, hydrophobic solvent.

The two-phase gel composition possesses a viscosity which is greater than or equal to the viscosity of the first component (i.e., the gelled ester composition, gelled ether composition, gelled alcohol composition, gelled naturally-occurring fat and oil composition, or a combination thereof, the second component (the solvent), and the sum of the viscosity of the first and second components. In some embodiments, the two-phase gel composition possesses a viscosity which is slightly greater than or equal to the viscosity of the first component, the second component, and/or the sum of the first and second components. In other embodiments, the viscosity of the two-phase gel composition is substantially greater than the sum of the viscosity of each component. The two-phase gel composition may be in the form of a liquid, solid, semi-solid, or gel. Where the two-phase gel composition is the form of a gel, the gel may be a soft gel, a semi-solid gel, a hard gel, or a rubbery gel.

In some embodiments, the two-phase gel composition may be substantially free of phosphate compounds, although one or more of these compounds may be present in other embodiments. Similarly, some two-phase gel compositions are substantially free of any antioxidants, while other two-phase gel compositions may include one or more antioxidants.

In certain embodiments, the two-phase gel composition and the products made from the two-phase gel composition are semi-transparent, hazy, or opaque. In certain other embodiments, the two-phase gel composition and the products made from the two-phase gel composition are transparent or substantially transparent. In certain other embodiments, the two-phase gel composition and the products made from the two-phase gel composition are translucent. The two-phase gel composition and the products made from the two-phase gel composition each have numerous cosmetic, health and beauty, home care, and industrial applications.

The two-phase gel composition may optionally include additional components. The two-phase gel composition provides suspension stability to components which may be suspended therein and controlled release capabilities. In some embodiments, the two-phase gel composition may additionally include a suspended component. Examples of suitable suspended components include, but are not limited to, solids, non-hydrocarbon liquids, and gases which will disperse into the two-phase gel composition and remain substantially suspended or evenly dispersed therein. In some embodiments, the two-phase gel composition may additionally include an active ingredient. Examples of suitable active ingredients include, but are not limited to, sunscreens, antiperspirants, deodorants, perfumes, cosmetics, emollients, insect repellents, pesticides, herbicides, fungicides, plasticizers, insecticides, and medicaments. The amount of the additional component used in the two-phase gel composition depends upon the desired properties of the end product in which the two-phase gel composition is used.

As used herein, a gel refers to a two-phase colloidal system comprising a liquid and a solid in the form of a thickened liquid, semi-solid or solid. A gel also can refer to a composition that is either physically cross-linked by virtue of entangled polymer chains or by development of associative networks or insoluble domains or chemically cross-linked by virtue of covalent bonds such that it swells, but does not dissolve, in the presence of liquid. A gel typically is obtained by use of a gelling agent. The term "gelling agent" as used herein refers to a polymer dispersed in any suitable liquid, semi-solid, or solid material. The term "polymer" used herein includes both homopolymer and copolymer. A homopolymer is a polymer obtained by polymerizing one type of monomer, whereas a copolymer is a polymer obtained by polymerizing two or more types of monomers. "Block copolymer" refers to a copolymer in which like monomer units occur in relatively long, alternate sequences on a chain. The term "gel composition" as used herein refers to a gelling agent dispersed, dissolved, or swelled in a suitable liquid, semi-solid, or solid material.

The term "two-phase gel composition" as used herein refers to a two component system in which one component is a gelled component and the second component is a solvent. The use of the term two-phase gel composition is not intended to require that the gel composition have two separate physical phases. As used herein, the term two-phase gel composition maybe homogenous; (i.e., a single phase). In some embodiments, the two-phase gel composition does not separate back into the individual components used to make the two-phase gel composition. In other embodiments, the two-phase gel composition may have two, three, four, five or more phases. As used herein, the term "opaque" refers to the optical state of a medium whose molecular aggregation is such that light cannot pass through. Therefore, light transmission through an opaque medium is substantially close to zero. On the other hand, the term "transparent" refers to the optical state of a medium through which light can pass through so that an object can be seen through it. As used herein, the term "transparent" includes any optical state which is not opaque. A medium is considered transparent even if only a small fraction of light passes through it. Thus, a clear gel and a translucent gel are considered transparent.

The gelled ester, gelled ether, gelled alcohol, or gelled naturally-occurring fat and oil component is the sole source of polymer for the two-phase gel composition. This component may also be referred to as a "gel base", a "gelled base", or a "gelled component". One or more gelled esters, gelled ethers, gelled alcohols, or gelled naturally-occurring fats and oils may be used in embodiments of the invention to form the two-phase gel composition. While not absolutely necessary, it is preferred that the gelled ester, gelled ether, gelled alcohol, or gelled naturally-occurring fat and oil component is a relatively polar polymer concentrate with a relatively low viscosity. In some embodiments, the gel led ester, gelled ether, gelled alcohol, or gelled naturally-occurring fat and oil component is a fluid it room temperature. Although the gelled ester, gelled ether, gelled alcohol, and gelled naturally-occurring fat and oil component may be in the solid phase, the gelled component is preferably in the form of a liquid or semi-solid for ease of handling.

The selection of the gelled ester, gelled ether, gelled alcohol, or gelled naturally-occurring fat and oil component used in the two-phase gel composition depends on a variety of factors. Such factors include, but are not limited to, the desired properties of the two-phase gel composition such as the viscosity, the desired properties of the end product in which the two-phase gel composition may be incorporated such as the viscosity, the processing temperature, the mixing capabilities, the desirability of raw materials, and the like.

The amount of the gelled ester, gelled ether, gelled alcohol, or gelled naturally-occurring fats and oil component present in the two-phase gel composition depends upon the desired properties of the two-phase gel composition such as the desired viscosity, the desired properties of the end product in which the two-phase gel composition may be incorporated such as the desired viscosity, the processing temperature, the mixing capabilities, and the like.

In some embodiments, a small amount of the gelled ester, gelled ether, gelled alcohol, or gelled naturally-occurring fat and oil component may be used to thicken the solvent Component. In some embodiments, the amount of the gelled ester, gelled ether, gelled alcohol, or gelled naturally-occurring fat and oil component present in the two-phase gel composition may range from about 5% to about 95% by weight of the two-phase gel composition. In certain other embodiments, the gelled ester, gelled ether, gelled alcohol, or gelled naturally-occurring fat and oil component is present in an amount from about 5% to about 60% by weight of the two-phase gel composition. In other embodiments, the gelled ester, gelled ether, gelled alcohol, or gelled naturally-occurring fat and oil component is present in an amount from about 10% to about 40% by weight of the two-phase gel composition. In still other embodiments, the gelled ester, gelled ether, gelled alcohol, or gelled naturally-occurring fat and oil component is present in an amount from about 20% to about 40% by weight of the two-phase gel composition.

The gelled ester, gelled ether, gelled alcohol, and gelled naturally-occurring fat and oil compositions and methods for making these compositions are described in detail in U.S. application Ser. No. 09/419,571 filed on Oct. 18, 1999, which is incorporated herein by reference. In some embodiments, a block copolymer capable of forming a three-dimensional network through physical cross-linking is used as the gelling agent for forming the gelled ester, gelled ether, gelled alcohol, and gelled naturally-occurring fat and oil compositions. Suitable block copolymers include at least one rigid block and one elastomeric block.

The rigid block typically is composed of polystyrene, polyethylene, polyvinyl chloride, phenolics, and the like; the elastomeric block may be composed of ethylene/butadiene copolymers, polyisoprene, polybutadiene, ethylene/propylene copolymers, ethylene-propylene/diene copolymers, and the like. As such, suitable diblock copolymers include, but are not limited to, styrene-ethylene/propylene copolymers, styrene-ethylene/butadiene copolymers, styrene-isoprene copolymers, styrene-butadiene copolymers and mixtures thereof.

Each polymer chain includes two rigid blocks at either end and a middle block which is elastomeric. This is a preferred triblock copolymer structure, although a triblock copolymer with two elastomeric end blocks and a rigid middle block also can be used. Suitable triblock copolymers include, but are not limited to, styrene-ethylene/propylene-styrene copolymers, styrene-ethylene/butadiene-styrene copolymers, styrene-isoprene-styrene copolymers, styrene-butadiene-styrene copolymers and mixtures thereof. Multi-block copolymers are similar to diblock copolymers or triblock copolymers, except that the multiple block copolymers include additional elastomeric blocks and/or rigid blocks.

In addition to the linear chain structure, branched homopolymers or copolymers also may be used to form the gelled ester, gelled ether, gelled alcohol, and gelled naturally-occurring fat and oil compositions. Suitable branched homopolymers or copolymers include, but are not limited to, radial and star polymers. It should be noted that one or more functional groups may be grafted onto the chain of any of the aforementioned polymers. In other words, any of the above polymers may be modified by grafting. Suitable functional groups for grafting depend on the desired properties. For example, one or more ester groups, silane groups, silicon-containing groups, maleic anhydride groups, acrylamide groups, and acid groups may be grafted. In addition to grafting, the above polymers may be hydrogenated to reduce unsaturation before they are used as gelling agents.

Numerous commercially available block copolymers may be used to form the gelled ester compositions, gelled ether compositions, gelled alcohol compositions, and gelled naturally-occurring fats and oil compositions. For example, various grades of copolymers sold under the trade name of Kraton® from Kraton Company can be used as a gelling agent for forming the gelled ester, gelled ether, gelled alcohol, and gelled naturally-occurring fat and oil compositions. In addition, copolymers sold under the trade name of Vector® available from Dexco, and Septon® from Kuraray, Tuftec® available from Asahi, and Solprene® available from GIRSA Industrias Negromex, S.A. de C.V. (INSA) also may be used as a gelling agent for forming the gelled ester, gelled ether, gelled alcohol, and gelled naturally-occurring fat and oil compositions. U.S. Pat. Nos. 5,221,534, 5,578,089, and 5,879,694 disclose block copolymers which may be used in embodiments of the invention. The disclosures of the three patents are incorporated by reference in their entirety herein. Table 1 lists some commercially available block copolymers which may be used to form the gelled ester compositions, gelled ether compositions, gelled alcohol compositions, and gelled naturally-occurring fat and oil compositions. It is noted that additional suitable block copolymers may include, but are not limited to, polystyrene/polyester, polyether/polyamide, polyether/polyester, polyester/polyamide, polyether/polyurethane, polyester/polyurethane, poly(ethylene oxide)/poly(propylene oxide), nylon/rubber, and polysiloxane/polycarbonate.

TABLE 1

| Copolymer | Block Type | Polystyrene Content (%) | Comment |
|---|---|---|---|
| Kraton® G1702 | SEP | 28 | hydrogenated diblock |
| Kraton® G1701 | SEP | 37 | hydrogenated diblock |
| Kraton® G1780 | SEP | 7 | hydrogenated star polymer |
| Kraton® G1650 | SEBS | 30 | hydrogenated triblock |
| Kraton® G1652 | SEBS | 30 | hydrogenated triblock |
| Kraton® D1101 | SBS + SP | 31 | unsaturated triblock and diblock mixture (85:15) |
| Kraton® D1102 | SBS + SP | 28 | unsaturated triblock + diblock (85:15) |
| Kraton® D1133 | SBS + SP | 35 | unsaturated triblock + diblock (66:34) |
| Kraton® G1901 | SEBS | 30 | triblock (hydrogenated and functionally grafted with 1.7% of maleic anhydride) |
| Septon® 1001 | SEP | 35 | hydrogenated diblock |
| Vector® 6030 | SP | 30 | unsaturated diblock |
| Vector® 8550 | SBS | 29 | unsaturated triblock |
| Vector® 2518P | SBS | 31 | unsaturated triblock |
| Solprene® 1430 | SB | 40 | unsaturated diblock |
| Kraton® D1160 | SIS + SI | 18 | unsaturated triblock + diblock (80:20) |

Note: SEP denotes to styrene/ethylene/propylene copolymers
SEBS denotes to styrene/ethylene/butylene/styrene copolymers
SB denotes to styrene/butadiene copolymers
SBS denotes to styrene-butadiene-styrene copolymers
SI denotes styrene/isoprene copolymers
SIS denotes styrene/isoprene/styrene copolymers The gelled ester composition used in the two-phase gel composition is obtained by gelling at least two components. The first component is an ester compound. The second component may be a polymer compound selected from the group consisting of a triblock copolymer, a star polymer, a radial polymer, a multi-block copolymer, or combinations thereof. Optionally, the gelled ester composition may further include one or more diblock copolymers. When a diblock copolymer is used along with one of triblock copolymers, star polymers, radial polymers, and multi-block copolymers, the resulting gel composition is substantially free of mineral oils. In some embodiments, the gelled ester composition may be substantially free of phosphate compounds, although one or more of these compounds may be present in other embodiments.

Any ester compound may be used in embodiments of the invention to obtain the gelled ester composition. An ester is defined as a compound that includes one or more carboxylate groups: R—COO—, where R is hydrogen, hydrocarbyl, phenyl, methoxyphenyl, alkylphenyl, substituted alkyl, substituted phenyl, or other organic radicals. Suitable esters include monoesters, diesters, triesters, etc. For example, one class of suitable esters that can be gelled is represented by the following formulas:

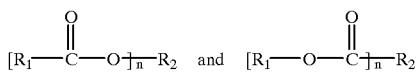

where n=1, 2, 3, and 4, and $R_1$ includes hydrogen, hydrocarbyl, phenyl, methoxyphenyl, alkylphenyl, substituted alkyl, and substituted phenyl; and $R_2$ includes hydrogen, hydrocarbyl, phenyl, methoxyphenyl, alkylphenyl, substituted alkyl, substituted phenyl, alkylene, phenylene, substituted alkylene, substituted phenylene, etc. It is noted that a suitable group for $R_2$ depends on whether n is 1, 2, 3, or 4.

Another class of suitable esters that may be gelled to obtain the gelled ester composition is represented by the following formula:

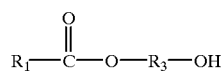

where $R_3$ includes alkylene, phenylene, substituted alkylene, and substituted phenylene.

Still another class of suitable esters that may be gelled to obtain the gelled ester composition is represented by the following formula:

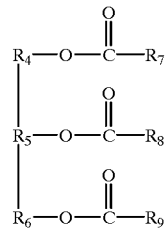

where $R_4$, $R_5$, and $R_6$ individually include alkylene, phenylene, substituted alkylene, and substituted phenylene; $R_7$, $R_8$, and $R_9$ individually include hydrogen, hydrocarbyl, phenyl, methoxyphenyl, alkylphenyl, substituted alkyl, and substituted phenyl.

Preferred esters and their chemical formulas are listed in Table 2.

TABLE 2

| Chemical Name | Chemical Formula |
|---|---|
| Isononyl Isononanoate | $C_8H_{17}-C(=O)-O-C_9H_{19}$ |
| Isopropyl Palmitate | $C_{15}H_{31}-C(=O)-O-C_3H_7$ |
| $C_{12-15}$ alkyl benzoate | Ph-C(=O)-O-$C_{12-15}$ |
| Myristyl Neopentanoate | $C_7H_{15}-C(=O)-O-(CH_2)_{13}-CH_3$ |
| Tridecyl Salicylate | (2-OH-Ph)-C(=O)-O-$C_{13}H_{27}$ |
| Octyl Methoxycinnamate | $CH_3-O-C_6H_4-CH=CH-C(=O)-O-CH_2-C_7H_{13}$ |
| Propylene glycol dicaprylate/caprate | $CH_3-(CH_2)_6-C(=O)-O-CH_2-CH(CH_3)-O-C(=O)-(CH_2)_6-CH_3$ |

TABLE 2-continued

| Chemical Name | Chemical Formula |
|---|---|
| Pentaerythrityl tetraisostearate | 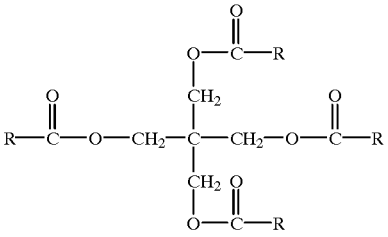<br>(Represents fatty acid radicals derived from coconut oil) |
| Trimethylolpropane triisostearate | 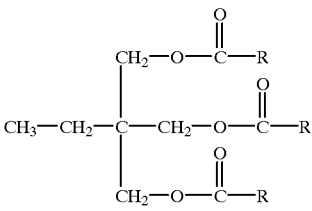<br>(Represents fatty acid radicals derived from coconut oil) |
| Glyceryl isostearate | 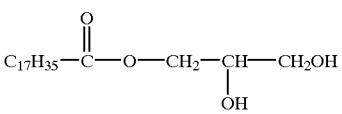 |
| Diisononyl adipate | 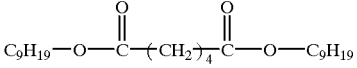 |
| Trioctyldodecyl citrate | 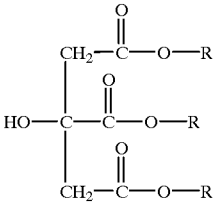<br>(R is octyl dodecyl) |
| Isopropyl myristate | 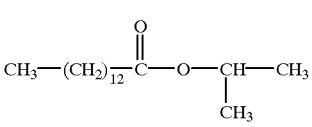 |

Other suitable esters include, but are not limited to, the following compounds: Acefylline Methylsilanol Mannuronate; Acetaminosalol; Acetylated Cetyl Hydroxyprolinate; Acetylated Glycol Stearate; Acetylated Sucrose Distearate; Acetylmethionyl Methylsilanol Elastinate; Acetyl Tributyl Citrate; Acetyl Triethyl Citrate; Acetyl Trihexyl Citrate; *Aleurites Moluccana* Ethyl Ester; Allethrins; Allyl Caproate; Amyl Acetate; Amyl Benzoate; Amyl Salicylate; Arachidyl Behenate; Arachidyl Glycol Isostearate; Arachidyl Propionate; Ascorbyl Dipalmitate; Ascorbyl Palmitate; Ascorbyl Stearate; Aspartame; Batyl Isostearate; Batyl Stearate; Bean Palmitate; Behenyl Beeswax; Behenyl Behenate; Behenyl Benzoate; Behenyl Erucate; Behenyl Isostearate; Behenyl/ Isostearyl Beeswax; 1,2,4-Benzenetriacetate; Benzoin (Styrax Bensoin) Gum; Benzoxiquine; Benzyl Acetate; Benzyl Benzoate; Benzyl Cinnamate; Benzyl Hyaluronate; Benzyl Laurate; Benzyl Nicotinate; Benzylparaben; Benzyl Salicylate; Beta-Sitosteryl Acetate; *Borago Officinalis* Ethyl Ester; Butoxyethyl Acetate; Butoxyethyl Nicotinate; Butoxyethyl Stearate; Butyl Acetate; Butyl Acetyl Ricinoleate; Butyl Benzoate; Butyl Benzyl Phthalate; 2-t-Butylcyclohexyl Acetate; Butylene Glycol Dicaprylate/ Dicaprate; Butylene Glycol Montanate; Butyl Ester of Ethylene/MA Copolymer; Butyl Ester of PVM/MA Copolymer; Butylglucoside Caprate; Butyl Isostearate; Butyl Lactate; Butyl Methacrylate; Butyl Myristate; Butyloctyl Beeswax; Butyloctyl Benzoate; Butyloctyl Candelillate; Butyloctyl Oleate; Butyloctyl Salicylate; Butyl Oleate; Butyl PABA; Butylparaben; Butyl Phthalyl Butyl Glycolate; Butyl Stearate; Butyl Thioglycolate; Butyroyl Trihexyl Citrate; C18–36 Acid Glycol Ester; C12–20 Acid PEG-8 Ester; Caffeine Benzoate; Calcium Pantetheine Sulfonate; Calcium Stearoyl Lactylate; C18–28 Alkyl Acetate; C18–38 Alkyl Beeswax; C30–50 Alkyl Beeswax; C20–40 Alkyl Behenate; C18–38 Alkyl C24–54 Acid Ester; C-8 Alkyl Ethyl Phosphate; C18–38 Alkyl Hydroxystearoyl Stearate; C12–13 Alkyl Lactate; C12–15 Alkyl Lactate; C12–13 Alkyl Octanoate; C12–15 Alkyl Octanoate; C12–15 Alkyl Salicylate; C18–36 Alkyl Stearate; C20–40 Alkyl Stearate; C30–50 Alkyl Stearate; C40–60 Alkyl Stearate; Caproyl Ethyl Glucoside; Capryloyl Salicylic Acid; Caprylyl Butyrate; Castor Oil Benzoate; C10–30 Cholesterol/Lanoster-ol Esters; Cellulose Acetate; Cellulose Acetate Butyrate; Cellulose Acetate Propionate; Cellulose Acetate Propionate Carboxylate; Ceteareth-7 Stearate; Cetearyl Behenate; Cetearyl Candelillate; Cetearyl Isononanoate; Cetearyl Octanoate; Cetearyl Palmitate; Cetearyl Stearate; Cetyl Acetate; Cetyl Acetyl Ricinoleate; Cetyl Caprylate; Cetyl C12–15-Pareth-9 Carboxylate; Cetyl Glycol Isostearate; Cetyl Isononanoate; Cetyl Lactate; Cetyl Laurate; Cetyl Myristate; Cetyl Octanoate; Cetyl Oleate; Cetyl Palmitalte; Cetyl PCA; Cetyl PPG-2 Isodeceth-7 Carboxylate; Cetyl Ricinoleate; Cetyl Ricinoleate Benzoate; Cetyl Stearate; C16–20 Glycol Isostearate; C20–30 Glycol Isostearate; C14–16 Glycol Palmitate; Chimyl Isostearate; Chimyl Stearate; Chlorogenic Acids; Cholesteryl Acetate; Cholesteryl/Behenyl/Octyldodecyl Lauroyl Glutamate; Cholesteryl Butyrate; Cholesteryl Dichlorobenzoate; Cholesteryl Hydroxystearate; Cholesteryl Isostearate; Cholesteryl Isostearyl Carbonate; Cholesteryl Lanolate; Cholesteryl Macadamiate; Cholesteryl Nonanoate; Cholesteryl/Octyldodecyl Lauroyl Glutamate; Cholesteryl Oleate; Cholesteryl Stearate; Cinnamyl Acetate; Cinoxate; Citronellyl Acetate; Coco-Caprylate/Caprate; Coco Rapeseedate; Cocoyl Ethyl Glucoside; Copper PCA Methylsilanol; *Corylus Avellanna* Ethyl Ester; C12–15 Pareth-9 Hydrogenated Tallowate; C11–15 Pareth-3 Oleate; C12–15 Pareth-12 Oleate; C11–15 Pareth-3 Stearate; C11–15 Pareth-12 Stearate; Decyl Isostearate; Decyl Myristate; Decyl Oleate; Decyl Succinate; DEDM Hydantoin Dilaurate; Dextrin Behenate; Dextrin Laurate; Dextrin Myristate; Dextrin Palmitate; Dextrin Stearate; Diacetin; Dibutyl Adipate; Dibutyl Oxalate; Dibutyl Phthalate; Dibutyl Sebacate; Di-C12–15 Alkyl Adipate; Di-C12–15 Alkyl Fumarate; Di-C12–13 Alkyl Malate; Di-C12–13 Alkyl Tartrate; Di-C14–15 Alkyl Tartrate; Dicapryl Adipate; Dicaprylyl Maleate; Dicetearyl Dimer Dilinoleate; Dicetyl Adipate; Dicetyl Thiodipropionate; Dicocoyl Pentaerythrilyl Distearyl Citrate; Diethoxyethyl Succinate; Diethyl Acetyl Aspartate; Diethylaminoethyl Cocoate; Diethylaminoethyl PEG-5 Cocoate; Diethylaminoethyl PEG-5 Laurate; Diethylaminoethyl Stearate; Diethyl Aspartate; Diethylene Glycol Dibenzoate; Diethylene Glycol Diisononanoate; Diethylene Glycol Dioctanoate; Diethylene Glycol Dioctanoate/Diisononanoate; Diethyl Glutamate; Diethyl Oxalate; Diethyl Palmitoyl Aspartate; Diethyl Phthalate; Diethyl Sebacate; Diethyl Succinate; Digalloyl Trioleate; Diglyceryl Stearate Malate; Dihexyl Adipate; Dihexyldecyl Lauroyl Glutamate; Dihydroabietyl Behenate; Dihydroabietyl Methacrylate; Dihydrocholesteryl Butyrate; Dihydrocholesteryl Isostearate; Dihydrocholesteryl Macadamiate; Dihydrocholesteryl Nonanoate; Dihydrocholesteryl Octyldecanoate; Dihydrocholesteryl Oleate; Dihydrogenated Palmoyl Hydroxyethylmonium Methosulfate; Dihydrogenated Tallow Phthalate; Dihydrophytosteryl Octyldecanoate; Dihydroxyethylamino Hydroxypropyl Oleate; Dihydroxyethyl Soyamine Dioleate; Diisobutyl Adipate; Diisobutyl Oxalate; Diisocetyl Adipate; Duisodecyl Adipate; Diisopropyl Adipate; Diisopropyl Dimer Dilinoleate; Diisopropyl Methyl Cinnamate; Diisopropyl Oxalate; Diisopropyl Sebacate; Diisostearamidopropyl Epoxypropylmonium Chloride; Diisostearoyl Trimethylolpropane Siloxy Silicate; Diisostearyl Adipate; Diisostearyl Dimer Dilinoleate; Diisostearyl Fumarate; Diisostearyl Glutarate; Diisostearyl Malte; Dilaureth-7 Citrate; Dilauryl Thiodipropionate; Dimethicone Copolyol Acetate; Dimethicone Copolyol Adipate; Dimethicone Copolyol Almondate; Dimethicone Copolyol Beeswax; Dimethicone Copolyol Behenate; Dimethicone Copolyol Benzoate; Dimethicone Copolyol Borageate; Dimethicone Copolyol Cocoa Butterate; Dimethiccne Copolyol Dhupa Butterate; Dimethicone Copolyol Hydroxystearate; Dimethicone Copolyol Isostearate; Dimethicone Copolyol Kokum Butterate; Dimethicone Copolyol Lactate; Dimethicone Copolyol Laurate; Dimethicone Copolyol Mango Butterate; Dimethicone Copolyol Meadowfoamate; Dimethicone Copolyol Mohwa Butterate; Dimethicone Copolyol Octyldodecyl Citrate; Dimethicone Copolyol Olivate; Dimethicone Copolyol Phthalate; Dimethicone Copolyol Sal Butterate; Dimethicone Copolyol Shea Butterate; Dimethicone Copolyol Stearate; Dimethicone Copoly Undecylenate; Dimethiconol Beeswax; Dimethiconol Behenate; Dimethiconol Borageate; Dimethiconol Dhupa Butterate; Dimethiconol Fluoroalcohol Dillnoleic Acid; Dimethiconol Hydroxystearate; Dimethiconol Illipe Butterate; Dimethiconol Isostearate; Dimethiconol Kokum Butterate; Dimethiconol Lactate; Dimethiconol Mohwa Butterate; Dimethiconol Sal Butterate; Dimethiconol Stearate; Dimethyl Adipate; Dimethylaminoethyl Methacrylate; Dimethyl Brassylate; Dimethyl Cystinate; Dimethyl Glutarate; Dimethyl Maleate; Dimethyl Oxalate; Dimethyl Phthalate; Dimethyl Succinate; Dimyristyl Tartrate; Dimyristyl Thiodipropionate; Dinonoxynol-9 Citrate; Dioctyl Adipate; Dioctyl Butamido Triazone; Dioctyl Dimer Dilinoleate; Dioctyldodeceth-2 Lauroyl Glutamate; Dioctyldodecyl Adipate; Dioctyldodecyl Dimer Dilinoleate; Dioctyldodecyl Dodecanedioate; Dioctyldodecyl Fluoroheptyl Citrate; Dioctyldodecyl Lauroyl Glutamate; Dioctyldodecyl Stearoyl Dimer Dilinoleate; Dioctydodecyl Stearoyl Glutamate; Diocty Fumarate; Dioctyl Malate; Dioctyl Maleate; Dioctyl Phthalate; Dioctyl Sebacate; Dioctyl Succinate; Dioleoyl Edetolmonium Methosulfate; Dipalmitoyl Hydroxyproline; Dipentaerythrityl Hexacaprylate/Hexacaprate; Dipentaerythrityl Hexaheptanoate/Hexacaprylate/Hexacaprate; Dipentaerythrityl Hexahydroxystearate; Dipentaerythrityl Hexahydroxystearate/Stearate/Rosinate; Dipentaerythrityl Hexaoctanoate/Behenate; Dipentaerythrityl Pentahydroxystearate/Isostearate; Diphenyl Carbomethoxy Acetoxy Naphthopyran; Dipropyl Adipate; Dipropylene Glycol Caprylate; Dipropylene Glycol Dibenzoate; Dipropylene Glycol Salicylate; Dipropyl Oxalate; Disodium Laureth-7 Citrate; Disodium PEG-5 Laurylcitrate Sulfosuccinate; Disodium PEG-8 Ricinosuccinate; Disodium Succinoyl Glycyrrhetinate; Disodium 2-Sulfolaurate; Disteareth-2 Lauroyl Glutamate; Disteareth-5 Lauroyl Glutamate; Distearyl Thiodipropionate; Ditallowoylethyl Hydroxyethylmonium Methosulfate; Ditridecyl Adipate; Ditridecyl Dimer Dilinoleate; Ditridecyl Thiodipropionate; Dodecyl Gallate; Erucyl Arachidate; Erucyl Erucate; Erucyl Oleate; Ethiodized Oil; Ethoxydiglycol Acetate; Ethoxyethanol Acetate; Ethyl Acetate; Ethyl Almondate; Ethyl Apricot Kemelate; Ethyl Arachidonate; Ethyl Aspartate;

Ethyl Avocadate; EthAyl Benzoate; Ethyl Biotinate; Ethyl Butylacetylaminopropionate; Ethyl Cinnamate; Ethyl Cyanoacrylate; Ethyl Cycolhexyl Propionate; Ethyl Digydroxypropyl PABA; Dethyl Diisopropylcinnamate; Ethylene Brassylate; Ethylene Carbonate; Ethy Ester of Hydrolyzed Animal Protein; Ethyl Ester of Hydrolyzed Keratin; Ethyl Ester of Hydrolyzed Silk; Ethyl Ester of PVM/MA Copolymer; Ethyl Ferulate; Ethyl Glutamate; Ethyl Isostearate; Ethyl Lactate; Ethyl Laurate; Ethyl Linoleate; Ethyl Linolenate; Ethyl Niethacrylate; Ethyl Methoxycinnamate; Ethyl Methylphenylglycidate; Ethyl Minkate; Ethyl Morrhuate; Ethyl Myristate; Ethyl Nicotinate; Ethyl Oleate; Ethyl Olivate; Ethyl PABA Ethyl Palmitate; Ethylparaben; Ethyl PCA; Ethyl Pelargonate; Ethyl Persate; Ethyl Phenylacetate; Ethyl Ricinoleate; Ethyl Serinate; Ethyl Stearate; Ethyl Thioglycolate; Ethyl Urocanate; Ethyl Wheat Germate; Ethyl Ximenynate; Ltocrylene; Famesyl Acetate; Galactonolactone; Galbanum (*Ferula Galbaniflua*) Oil; Gamma-Nonalacione; Geranyl Acetate; Glucarolactone; Glucose Glutamate; Glucose Pentaacetate; Glucuronolactone; Glycereth-7 Benzoate; Glycereth-7 Diisononanoate; Glycereth-8 Hydroxystearate; Glycereth-5 Lactate; Glycereth-25 PCA Isostearate; Glycereth-7 Triacetate; Glyceryl Triacetyl Hydroxystearate; Glyceryl Triacetyl Ricinoleate; Glycolamide Stearate; Glycol/Butylene Glycol Montanate; Glycol Catearate; Glycol Dibehenate; Glycol Dilaurate; Glycol Dioctanoate; Glycol Dioleate; Glycol Distearate; Glycol Ditallowate; Glycol Hydroxystearate; Glycol Montanate; Glycol Octanoate; Glycol Oleate; Glycol Palmitate; Glycol Ricinoleate; Glycol Salicylate; Glycol Stearate; Glycol Stearate SE; Glycyrrhetinyl Stearate; Hexacosyl Glycol Isostearate; Hexanediol Beeswax; Hexanediol Distearate; Hexanetriol Beeswax; Hexyldecyl Benzoate; Hexyldecyl Ester of Hydrolyzed Collagen; Hexyldecyl Isostearate; Hexyldecyl Laurate; Hexyldecyl Octanoate; Hexyldecyl Oleate; Hexyldecyl Palmitate; Hexyldecyl Stearate; Hexyldodecyl Salicylate; Hexyl Isostearate; Hexyl Laurate; Hexyl Nicotinate; Homosalate; Hydrogenated Castor Oil Hydroxystearate; Hydrogenated Castor Oil Isostearate; Hydrogenated Castor Oil Lauirate; Hydrogenated Castor Oil Stearate; Hydrogenated Castor Oil Triisostearate; Hydrogenated Methyl Abietate; Hydrogenated Rosin; Hydroquinone PCA; Hydroxycetyl Isostearate; Hydroxyoctacosanyl Hydroxystearate; Inositol Hexa-PCA; Iodopropynyl Butylcarbamate; Isoamyl Acetate; Isoamyl Laurate; Isoamyl p-Methoxycinnamate; Isobutyl Acetate; Isobutylated Lanolin Oil; Isobutyl Benzoate; Isobutyl Myristate; Isobutyl Palmitate; Isobutylparaben; Isobutyl Pelargonate; Isobutyl Stearate; Isobutyl Tallowate; Isoceteareth-8 Stearate; Isoceteth-10 Stearate; Isocetyl Behenate; Isocetyl Isodecanoate; Isocetyl Isostearate; Isocetyl Laurate; Isocetyl Linoleoyl Stearate; Isocetyl Myristate:, Isocetyl Octanoate; Isocetyl Palmitate; Isocetyl Salicylate; Isocetyl Stearate; Isocetyl Stearoyl Stearate; Isodeceth-2 Cocoate; Isodecyl Citrate; Isodecyl Cocoate; Isodecyl Hydroxystearate; Isodecyl Isononanoale; Isodecyl Laurate; Isodecyl Myristate; Isodecyl Neopentanoate; Isodecyl Octanoate; Isodecyl Oleate; Isodecyl Palmitate; Isodecylparaben; Isodecyl Salicylate; Isodecyl Stearate; Isohexyl Laurate; Isohexyl Neopentanoate; Isohexyl Palmitate; Isolauryl Behenate; Isomerized Joj oba Oil; Isononyl Ferulate; Isooctyl Thioglycolate; Isopropyl Acetate; Isopropyl Arachidate; Isopropyl Avocadate; Isopropyl Behenate; Isopropyl Benzoate; Isopropylbenzyl Salicylate; Isopropyl Citrate; Isopropyl C12–15-Pareth-9 Carboxylate; Isopropyl Hydroxystearate; Isopropyl Isostearate; Isopropyl Jojobate; Isopropyl Lanolate; Isopropyl Laurate; Isopropyl Linoleate; Isopropyl Myristate; Isopropyl Oleate; Isopropylparaben; Isopropyl PPG-2-Isodeceth-7 Carboxylate; Isopropyl Ricinoleate; Isopropyl Sorbate; Isopropyl Stearate; Isopropyl Tallowate; Isopropyl Thioglycolate; Isosorbide Laurate; Isosteareth-10 Stearate; Isostearyl Avocadate; Isostearyl Behenate; Isostearyl Benzoate; Isostearyl Erucate; Isostearyl Isononanoate; Iscstearyl Isostearate; Isostearyl Isostearoyl Stearate; Isostearyl Lactate; Isostearyl Laurate; Isostearyl Myristate; Isostearyl Neopentanoate; Isostearyl Octanoate; Isostearyl Palmitate; Isostearyl Stearoyl Stearate; Isotridecyl Isononanoate; Isotridecyl Laurate; Isotridecyl Myristate; Jojoba (*Buxus Chinensis*) Oil; Jojoba Esters; Kojic Dipalmitate; Laneth-9 Acetate; Laneth-10 Acetate; Laneth-4 Phosphate; Lanolin Linoleate; Lanolin Ricinoleate; Laureth-2 Acetate; Laureth-2 Benzoate; Laureth-6 Citrate; Laureth-7 Citrate; Laureth-2 Octanoate; Laureth-7 Tartrate; Lauroyl Ethyl Glucoside; Lauroyl Lactylic Acid; Lauryl Behenate; Lauryl Cocoate; Lauryl Isostearate; Lauryl Lactate; Lauryl Methacrylate; Lauryl Myristate; Lauryl Octanoate; Lauryl Oleate; Lauryl Palmitate; Lauryl Stearate; Linalyl Acetate; Linoleyl Lactate; Madecassicoside; Mannitan Laurate; Mannitan Oleate; Menthyl Acetate; Menthyl Anthranilate; Menthyl Lactate; Menthyl PCA; Menthyl Salicylate; Methoxyisopropyl Acetate; Methoxy-PEG-7 Rutinyl Succinate; Methyl Acetate; Methyl Acetyl Ricinoleate; Methyl Anthranilate; Methyl Behenate; Methyl Benzoate; Methyl Caproate; Methyl Caprylate; Methyl Caprylate/Caprate; Methyl Cocoate; 6-Methyl Coumarin; Methyl Dehydroabietate; Methyl Dihydroabietate; Methyldihydrojasmonate; Methyl Gluceth-20 Benzoate; Methyl Glucose Dioleate; Methyl Glucose Isostearate; Methyl Glucose Laurale; Methyl Glucose Sesquicaprylate/Sesquicaprate; Methyl Glucose Sesquicocoate; Methyl Glucose Sesquiisostearate; Methyl Glucose Sesquilaurate; Methyl Glucose Sesquioleate; Methyl Glucose Sesquistearate; Methyl Glycyrrhizate; Methyl Hydrogenated Rosinate; Methyl Hydroxystearate; Methyl Isostearate; Methyl Laurate; Methyl Linoleate; Methyl 3-Methylresorcylate; Methyl Myristate; Methyl Nicotinate; Methyl Oleate; Methyl Palmate; Methyl Palmitate; Methylparaben; Methyl Pelargonate; Methyl Ricinoleate; Methyl Rosinate; Methyl Salicylate; Methylsilanol Acetylmethionate; Methylsilaiaol Carboxymethyl Theophylline; Methylsilanol Carboxymethyl Theophylline Alginate; Methylsilanol Hydroxyproline; Methylsilanol Hydroxyproline Aspartate; Methylsilanol Mannuronate; Methylsilanol PCA; Methyl Soyate; Methyl Stearate; Methyl Thioglycolate; Monosaccharide Lactate Condensata; Myreth-3 Caprate; Myreth-3 Laurate; Myreth-2 Myristate; Myreth-3 Myristate; Myreth-3 Octanoate; Myreth-3 Palmitate; Myristoyl Ethyl Glucoside; Myristoyl Lactylic Acid; Myristyl Isostearate; Myristyl Lactate; Myristyl Lignocerate; Myristyl Myristate; Myristyl Octanoate; Myristyl Propionate; Myristyl Salicylate; Myristyl Stearate; Neopentyl Glycol Dicaprate; Neopentyl Glycol Dicaprylate/Dicaprate; Neopentyl Glycol Dicaprylate/ Dipelargonate/Dicaprate; Neopentyl Glycol Diheptanoate; Neopentyl Glycol Diisostearate; Neopentyl Glycol Dilaurate; Neopentyl Glycol Dioctanoate; Nonyl Acetate; Nopyl Acetate; Octacosanyl Glycol Isostearate; Octocrylene; Octyl Acetoxystearate; Octyl Benzoate; Octyl Caprylate/Caprate; Octyl Cocoate; Octyldecyl Oleate; Octyldodecyl Behenate; Octyldodecyl Benzoate; Octyldodecyl Erucate; Octyldodecyl Hydroxystearate; Octyldodecyl Isostearate; Octyldodecyl Lactate; Octyldodecyl Lanolate; Octyldodecyl Meadowfoamate; Octyldodecyl Myristate; Octyldodecyl Neodecanoate; Octyldodecyl Neopentanoate; Octyldodecyl Octanoate; Octyldodecyl Octyldodecanoate; Octyldodecyl Oleate; Octyldodecyl Olivate; Octyldodecyl Ricinoleate;

Octyldodecyl Stearate; Octyldodecyl Steroyl Stearate; Octyl Gallate; Octyl Hydroxystearate; Octyl Hydroxystearate Benzoate; Octyl Isononanoate; Octyl Isopalmitate; Octyl Isostearate; Octyl Laurate; Octyl Linoleayl Stearate; Octyl Methoxycinnamate; Octyl Myristate; Octyl Neopentanoate; Octyl Octanoate; Octyl Oleate; Octyl Palmitate; Octyl PCA; Octyl Pelagonate; Octyl Salicylate; Octyl Stearate; Oleoyl Ethyl Glucoside; Oleth-2 Benzoate; Oleyl Acetate; Oleyl Arachidate; Oleyl Erucate; Oleyl Ethyl Phosphate; Oleyl Lactate; Oleyl Lanolate; Oleyl Linoleate; Oleyl Myristate; Oleyl Oleate; Oleyl Phosphate; Oleyl Stearate; Oryzanol; Ozonized Jojoba Oil; Palmitoyl Carniline; Palmitoyl Inulin; Palmitoyl Myristyl Serinate; Pantethine; Panthenyl Ethyl Ester Acetate; Panthenyl Triacetate; PCA Glyceryl Oleate; Pea Palmitate; PEG-18 Castor Oil Dioleate; PEG-5 DMDM Hydantoin Oleate; PEG-15 DMDM Hydantoin Stearate; PEG-30 Dipolyhydroxystearate; PEG-20 Hydrogenated Castor Oil Isostearate; PEG-50 Hydrogenated Castor Oil Isostearate; PEG-20 Hydrogenated Castor Oil Triisostearate; PEG-20 Mannitan Laurate; PEG-20 Methyl Glucose Distearate; PEG-80 Methyl Glucose Laurate; PEG-20 Methyl Glucose Sesquicaprylate/Sescquicaprate; PEG-20 Methyl Glucose Sesquilaurate; PEG-5 Oleamide Dioleate; PEG-150 Pentaerythrityl Tetrastearate; PEG-3/PPG-2 Glyceryl/Sorbitol Hydroxystearate/Isostearate; PEG-4 Proline Linoleate; PEG-4 Proline Linolenate; PEG-8 Propylene Glycol Cocoate; PEG-55 Propylene Glycol Oleate; PEG-25 Propylene Glycol Stearate; PEG-75 Propylene Glycol Stearate; PEG-120 Propylene Glycol Stearate; PEG40 Sorbitol Hexaoleate; PEG-50 Sorbitol Hexaoleate; PEG-30 Sorbitol Tetraoleate Laurate; PEG-60 Sorbitol Tetrastearate; PEG-5 Tricapryl Citrate; PEG-5 Tricetyl Citrate; PEG-5 Trilauryl Citrate; PEG-5 Trimethylolpropane Trimyristate; PEG-5 Trimyristyl Citrate; PEG-5 Tristeaiyl Citrate; PEG-6 Undecylenate; Pentadecalacione; Pentaerythrityl Dioleate; Pentaerythrityl Distearate; Pentaerythrityl Hydrogenated Rosinate; Pentaerythrityl Isostearate/Caprate/Caprylate/Adipate; Pentaerythrityl Rosinate; Pentaerythrityl Stearate; Pentaerythrityl Stearate/Caprate/Caprylate/Adipate; Pentaerythrityl Stearate/lsostearate/Adipate/Hydroxystearate; Pentaerythrityl Tetraabietate; Pentaerythrityl Tetraacetate; Pentaerityl Tetrabehenate; Pentaerythrityl Tetrabenzoate; Petaerythrityl Tetracaprylate/Tetracaprate; Pentaerythrityl Tetracocoate; Pentaerythrityl Tetraisononanoate; Pentaerythrityl Tetralaurate; Pentaerythrityl Tetramyristate; Pentaerythrityl Tetraoctanoate; Pentaerythrityl Tetraoleate; Pentaerythrityl Tetrapelargonate; Petaerythrityl Tetrastearate; Pentaerythrityl Trioleate; Phenethyl Acetate; Phenolphthalein; Phenoxyethylparaben; Phenyl Benzoate; Phenylparaben; Phenyl Salicylate; Phylosteryl Macadamiate; Poloxamer 105 Benzoate; Poloxamer 182 Dibenzoate; Polycaprolactone; Polydimethylaminoethyl Methacrylate; Polyethylacrylate; Polyethylglutamate; Polyethylmethacrylate; Polymethyl Acrylate; Polymethylglutamate; Polysorbate 80 Acetate; Polyvinyl Acetate; Potassium Butylparaben; Potassium Deceth-4 Phosphate; Potassium Ethylparaben; Potassiuim Methylparaben; Potassium Propylparaben; PPG-2 Isoceleth-20 Acetate; PPG-14 Laureth-60 Alkyl Dicarbamate; PPG-20 Methyl Glucose Ether Acetate; PPG-20 Methyl Glucose Ether Distearate; PPG-2 Myristyl Ether Propionate; PPG-14 Palmeth-60 Alkyl Dicarbamate; PPG-15 Steryl Ether Benzoate; Pregnenolone Acetate; Propyl Acetate; Propyl Benzoate; Propylene Carbonate; Propylene Glocol Alginate; Propylene Glycol Behenate; Propylene Glycol Caprylate; Propylene Glycol Ceteth-3 Acetate; Propylene Glycol Ceteth-3 Propionate; Propylene Glycol Citrate; Propylene Glycol Cocoate; Propylene Glycol Dicaprate; Propylene Glycol Dicaproate; Propylene Glycol Dicaprylate; Propylene Glycol Dicocoate; Propylene Glycol Diisononanoate; Propylene Glycol Diisostearate; Propylene Glycol Dilaurate; Propylene Glycol Dioctanoate; Propylene Glycol Dioleate; Propylene Glycol Dipelargonate; Propylene Glycol Distearate; Propylene Glycol Diundecanoate; Propylene Glycol Hydroxystearate; Propylene GlycolIsoceteth-3 Acetate; Propylene Glycol Isostearate; Propylene Glycol Laurate; Propylene Glycol Linoleate; Propylene Glycol Linolenate; Propylene Glycol Myristate; Propylene Glycol Myristyl Ether Acetate; Propylene Glycol Oleate; Propylene Glycol Oleate SE; Propylene Glycol Ricinoleate; Propylene Glycol Soyate; Propylene Glycol Stearate; Propylene Glycol Stearate SE; Propyl Gallate; Propylparaben; Pyricarbate; Pyridoxine Dicaprylate; Pyridoxine Dilaurate; Pyridoxine Dioctenoate; Pyridoxine Dipalmitate; Pyridoxine Glycyrrhetinate; Pyridoxine Tripalmitate; Raffmose Myristate; Raffinose Oleate; Resorcinol Acetate; Retinyl Acetate; Retinyl Linoleate; Retinyl Palmitate; Retinyl Propionate; Riboflavin Tetraacetate; Ribonolaclone; Rosin Acrylate; Siloxanetriol Phytate; Silybum Marianum Ethyl Ester; Sodium Behenoyl Lactylate; Sodium Butylparaben; Sodium Caproyl Lactylate; Sodiumn Cocoyl Lactylate; Sodium Dilaureth-7 Citrate; Sodium Ethylparaben; Sodium Ethyl 2-Sulfolaurate; Sodium Isostearoyl Lactylate; Sodium Laureth-7 Tartrate; Sodium Lauroyl Lectylate; Sodium Methylparaben; Sodium Methyl 2-Sulfolaurate; Sodium Oleoyl Lactylate; Sodium Panteheine Sulfonate; Sodium Phytate; Sodium Propylparaben; Sodium Stearoyl Lactylate; Sorbeth-2 Cocoate; Sorbeth-6 Hexastearate; Sorbeth-3 Isostearate; Sorbityl Acetate; Soybean Palmitate; Soy Sterol Acetate; Stearamide DEA-Distearate; Stearamide DIBA-Stearate; Stearamide MEA-Stearate; Steareth-5 Stearate; Stearoyl Lactylic Acid; Stearyl Acetate; Stearyl Acetyl Glutamate; Stearyl Beeswax; Stearyl Behenate; Stearyl Benzoate; Stearyl Caprylate; Stearyl Citrate; Stearyl Erucate; Stearyl Glycol Isostearate; Stearyl Glycyrrhetinate; Stearyl Heptanoate; Stearyl Lactate; Stearyl Linoleate; Stearyl Octanoate; Stearyl Stearalte; Stearyl Stearoyl Stearate; Sucrose Acetate Isobutyrate; Sucrose Benzoate; Sucrose Cocoate; Sucrose Dilaurate; Sucrose Distearate; Sucrose Laurate; Sucrose Myristate; Sucrose Octaacetate; Sucrose Oleate; Sucrose Palmitate; Sucrose Polybehenate; Sucrose Polycottonseedate; Sucrose Polylaurate; Sucrose Polylinoleate; Sucrose Polypalmate; Sucrose Polysoyate; Sucrose Polystearate; Sucrose Ricinoleate; Sucrose Stearate; Sucrose Tetrastearate Triacetate; Sucrose Tribehenate; Sucrose Tristearate; Tallowoyl Ethyl Glucoside; Tannic Acid; TEA-Lauroyl Lactylate; Telmesteine; Terpineol Acetate; Tetrabutyl Phenyl Hydroxybenzoate; Tetradecyleicosyl Stearate; Tetrahexyldecyl Ascorbate; Tetrahydrofurfuryl Acetate. Tetrahydrofulrfryl Ricinoleate; Tocophersolan; Tocopheryl Acetate; Tocopheryl Linoleate; Tocopheryl Linoleate/Oleate; Tocopheryl Nicotinate; Tocopheryl Succinate; Tributyl Citrate; Tri-C12–13 Alkyl Citrate; Tri-C14–15 Alkyl Citrate; Tricaprylyl Citrate; Tridecyl Behenate; Tridecyl Cocoate; Tridec), Erucate; Tridecyl Isononanoate; Tridecyl Laurate; Tridecyl Myristate; Tridecyl Neopentanoate; Tridecyl Octanoate; Tridecyl Stearate; Tridecyl Stearoyl Stearate; Tridecyl Trimellitate; Triethyl Citrate; Triethylene Glycol hydrogenated Rosinate; Trihexyldecyl Citrate; Triisocetyl Citrate; Triisopropyl Citrate; Triisopropyl Trilinoleate; Triisostearyl Citrate; Triisostearyl Trilinoleate; Trilactin; Trilauryl Citrate; Trimethylolpropane Tricaprylate/Tricaprate; Trimethylolpropane Tricocoate; Trimethylolpropane Trilaurate; Trimethylalpropane Trioctanoate; Trimethylolpropane Tristearate; Trimethyl Pentanyl Diisobutyrate; Trioctyl Citrate;

Trioctyldodecyl Borate; Trictyl Trimellitate; Triole:yl Citrate; TriPABA Panthenol; Tripropylene Glycol Citrate; Tristearyl Citrate; Tristearyl Phosphate; Viny;l Acetate; and Yeast Palmitate.

The gelled ether composition used in the two-phase gel composition is obtained by gelling at least two components. The first component is an ether compound. The second component may be a polymer compound selected from the group consisting of a diblock copolymer, a triblock copolymer, a star polymer, a radial polymer, a multi-block copolymer, or combinations thereof. Generally, an ether compound is represented by the following formula:

$$R-O-R'$$

where R and R' individually include, but are not limited to, hydrocarbyl, phenyl, methoxyphenyl, alkylphenyl, substituted alkyl, substituted phenyl, etc. Preferred ethers include, but are not limited to, dicaprylyl ether and octyl methoxycinnamate. Dicaprylyl either is represented by the following chemical formula:

$$C_8H_{17}-O-C_8H_{17}$$

Other suitable ethers include, but are not limited to the following compounds: Anethole; p-Anisic Acid; Batyl Alcohol; Batyl Isostearate; Batyl Stearate; Benzylhemiformal; 1,3-Bis-(2,4-Diaminophenoxy) propane; Butoxyethyl Acetate; Butoxyethyl Nicotinate; Butoxyethyl Stearate; Butoxypropanol; 2-t-Butylcyclohexyloxybutanol; Butyl Glucoside; Butylglucoside Caprate; Butyl Methoxydibenzoylmethane; Caprylyl/Capryl Glucoside; Capsaicin; Carboxymethyl Chitin; Carboxymethyl Chitosan Succinamide; Carboxymethyl Dextran; Cetearyl Glucoside; Cetyl Glyceryl Ether; Cetyl-PG Hydroxyethyl Decanamide; Cetyl-PG Hydroxyethyl Palmitamide; Chimyl Alcohol; Chimyl Isostearate; Chimyl Stearate; Chlorphenesin; Cinoxate; Cocamidopropyl Lauryl Ether; Coceth-4 Glucoside; Coco-Glucoside; Dibenzylidene Sorbitol; Dicetyl Ether; Dichlorophenyl Imidazoidioxolan; Dimethicone Copolyol Butyl Ether; Dimethicone Copolyol Ethyl Ether; Dimethicone Copolyol Methyl Ether; Dimethyl Hexahydronaphthyl Dihydroxymethyl Acetal; Dimethyl Isosorbide; Dioleyl TocophLeryl Methylsilanol; Diosmine; Disodium Cetyl Phenyl Ether Disulfonate; Disodium Decyl Phenyl Ether Disulfonate; Disodium Lauryl Phenyl Ether Disulfonate; Distarch Glyceryl Ether; Distearyl Ether; Ethoxydiglycol Acetate; Ethoxyheptyl Bicyclooctanone; 7-Ethylbicyclooxazolidine; Ethyl Methoxycinnamate; Ethyl Methylphenylglycidate; Ethyl Phenethyl Acetal; Eucalyptol; Eugenol; Ferulic Acid; Glyceryl Octanoate Dimethoxycinnamate; Glycofurol; Hexamethylindanopyran; Hexamidine; Hexamidine Diparaben; Hexamidine Paraben; Hydrogenated Ethylbicycloheptane Guaiacol; p-Hydroxyanisole; Hydroxydecyl Maltitol; Hydroxyethyl Glyceryl Oleate/Stearate; Hydroxyethyl Palmityl Oxyhydroxypropyl Palmitamide; Hydroxyethyl Sorbitol; Hydroxymethoxybenzyl Pelargonamide; Hydroxypropyl Starch Phosphate; Hydroxystearyl Cetyl Ether; Isobutyl Methyl Tetrahydropyranol; Isoeugenol; Isolongifolene Epoxide; Isopropyl Hydroxycetyl Ether; Isostearamidopropyl Epoxypropyl Dimonium Chloride; Isostearyl Glyceryl Ether; Isostearyl Glyceryl Pentaerythrityl Ether; Lauryl Polyglyceryl-6 Cetearyl Glycol Ether; Melatonin; Menthone Glycerin Acetal; Methoxylndane; Methoxyisopropyl Acetate; Methoxymethylbutanol; Methoxypropylgluconamide; Methylal; Ethyl Eugenol; Methyl Hexyl Ether; Methylsilanol Ascorbate; Myristyl-PG Hydroxyethyl Decanamide; 4-Nitroguaiacol; Octoxyglycerin; Octoxyglyceryl Behenate; Octoxyglyceryl Palmitate; Octyl Glyceryl Palmitate; Oleyl Glyceryl Ether; Panthenyl Ethyl Ether; Panthenyl Ethyl Ether Acetate; Panthenyl Hydroxypropyl Steardimonium Chloride; PEG-3 2,2-Di-p-Phenylenediamine; PEG-4 Ditallow Ether; PEG-150 Pentaerythrityl Tetrastearate; p-Phenetidine; Phenoxyethanol; Phenoxyethylparaben; Phenoxyisopropanol; Polyglycerin-3; Polyglycerin-4; Polyglycerin-6; Polyglycerin-10; Polyglyceryl-3 Cetyl Ether; Polyglyceryl-3 Decyltetradecyl Ether; Polyglyceryl-3 Hydroxylauryl Ether; Polyglyceryl-2 Lanolin Alcohol Ether; Polyglyceryl-4 Lauryl Ether; Polyglyceryl-2 Oleyl Ether; Polyglyceryl-4 Oleyl Ether; Polyglyceryl Sorbitol; Polyvinyl Methyl Ether; Polyvinyl Stearyl Ether; PPG-9 Diglyceryl Ether; PPG-1-PEG-9 Lauryl Glycol Ether; Propylene Glycol Myristyl Ether; Quassin; Silanetriol Trehalose Ether; TEA-Lauryl Ether; Tetrahydrodiferuloyimethane; Thiodiglycol; Triclosan; Triethylene Glycol; Trihydroxypalmitamidohydroxypropyl Myristyl Ether; Trimethoxycaprylylsilane; Troxerutin; and Ubiquinone.

The gelled alcohol composition used in the two-phase gel composition is obtained by gelling at least two components. The first component is an alcohol compound. The second component may be a polymer compound selected from the group consisting of a diblock copolymer, a triblock copolymer, a star polymer, a radial polymer, a multi-block copolymer, and combinations thereof. Any alcohol as represented by the following formula may be gelled to obtain the gelled alcohol composition:

$$R-OH$$

where R represents any organic functional group which includes, but is not limited to, hydrocarbyl, phenyl, methoxyphenyl, alkylphenyl, substituted alkyl, substituted phenyl, etc. Preferred alcohols include, but are not limited to, isostearyl alcohol, and octyl dodecanol. Other suitable alcohols include, but are not limited to the following compounds: Abietyl Alcohol; Arachidyl Alcohol; Batyl Alcohol; Behenyl Alcohol; Benzyl Alcohol; Bishydroxyethyl Biscetyl Malonamide; Borneol; 2-t-Butylcyclohexyloxybutanol; Butyloctanol; C9–11 Alcohol; C12–13 Alcohol; C12–15 Alcohol; C12–16 Alcohol; C14–15 Alcohol; C-20–40 Alcohols; C30–50 Alcohols; C40–60 Alcohols; C18–38 Alkyl Hydroxystearoyl Stearate; Camphylcyclohexanol; Caproyl Sphingosine; Caprylic Alcohol; Caprylyl Glycol; CD Alcohol 19; Ceramide 1; Ceramide 2; Cermide 3; Ceramide 4; Ceramide 5; Ceramide 1A; Ceramide 611; Cetearyl Alcohol; Cetyl Alcohol; Cetylarachidol; Cetyl Glycol; C9–13 Fluoroalcohol; C14–18 Glycol; C15–18 Glycol; C18–30 Glycol; C20–30 Glycol; Chimyl Alcohol; Chlorphenesin; Cholelciferol; Cholesterol; Cinnamyl Alcohol; Citronellol; Coconut Alcohol; Decyl Alcohol; Decyltetradecanol; 7-Dehydrocholesterol; Dichlorobenzyl Alcohol; Dihydrocholesterol; Dihydrolanosterol; Dihydroxyacetone; Dihydroxyethylamino Hydroxypropyl Oleate; 2,6-Dimethyl-7-Octen-2-ol; Dimethyl Octynediol; Dimethyl Phenylpropanol; Dodecylhexadecanol; Dodecyltetradecanol; Ergocalciferol; Ethyl Hexanediol; Famesol; Galactonolactone; Geraniol; Glycyrrhetinic Acid; Glycyrrhizic Acid; Heptylundecanol; Hexacosyl Glycol; 3-Hexenol; Hexyl Alcohol; Hexyldecanol; Hexyldecyloctadecanol; Hexylene Glycol; Hinokitiol; Hydroabietyl Alcohol; Hydrogenated Ethylbicycloneplane Guaiacol; Hydrogenated Tallow Alcohol; Hydrolyzed Glycyrrhizinate; Hydroxycapric Acid; Hydroxycaproyl Phytosphingosine; Hydroxycaprylic Acid; Hydroxycaproyl Phytosphingosine; Hydroxyethyl Palmityl Oxyhydroxypropyl Palmitamide; Hydroxylauric Acid; Hydroxylauroyl Phytosphingosine; Hydroxymethyl Dioxoazabicyclooctane; Hydroxyproline; Hydroxystearyl Cetyl Ether; Jojoba Alcohol; Lactoyl Phytosphingosine; Lanolin Alcolhol; Lauryl Alcohol; Lauryl Glycol; Linalool; p-Menthan-7-ol; Menthol; Menthone Glycerin Acetal; 3-Methylamino-4-Nitrophenoxyethanol; Methyl Glycyrrhiziate; Methylsilanol Hydroxyproline; Myricyl Alcohol; Myristyl Alcohol; Nicotinyl Alcohol; Nicotinyl Tartrate; 3-Nitro-4-Aminophenoxyethanol; Octacosanyl Glycol; Octoxyglycerin; Octoxyglyceryl Behenate; Octyldodecanol; 2-Oeamido-1,3-Ociadecanediol; Oleyl Alcohol; Palm Alcohol; Palm Kernel Alcohol; Palmitamidohexadecanediol; Panthenol; Panthenyl Ethyl Ether; Panthenyl Hydroxypropyl Steardimonium Chloride; Pentadecyl Alcohol; Pentylene Glycol; Phenethyl Alcohol; Phenoxyethanol; Phenoxyisopropanol; Phenylisohexanol; Phenylpropanol; Phytosphingosine; Polyvinyl Alcohol; Propanediol; Propyl Alcohol; Propylene Glycol; Pyridoxine Glycyrrhetinate; Retinol; Ribonolactone; N-Stearoyl-Dihydroshingosine; Stearyl Alcohol; Stearyl Glycol; Tallow Alcohol; Terpineol; Tetradecyleicosanol; Tetradecyloctadecanol; Tetrahydrofurfuryl Alcohol; Tetramethyl Cyclopentene Butenol; Tetramethyl Decynediol; Tridecyl Alcohol:, Trimethylhexanol; Troxerutin; Undeceth-3; Undecylenyl Alcohol; and Undecylpentadecanol.

The gelled naturally-occurring fats and oil composition used in the two-phase gel composition is obtained by gelling at least two components. The first component is a naturally-occurring fat and oil compound. The second component may be a polymer compound selected from the group consisting of a diblock copolymer, a triblock copolymer, a star polymer, a radial polymer, a multi-block copolymer, and combinations thereof.

"Naturally-occurring fats and oils" often refer to the glyceryl esters of fatty acids (i.e., triglycerides) normally found in animal or plant tissues, including those which have been hydrogenated to reduce or eliminate unsaturation. Naturally occurring fats and oils include vegetable oils such as linseed oil, soybean oil, sunflower seed oil, corn oil, sesame oil, olive oil, castor oil, coconut oil, palm oil, peanut oil, jojoba oil, and *macadamia* nut oil.

Selected naturally-occurring fats and oils are represented by the following formula:

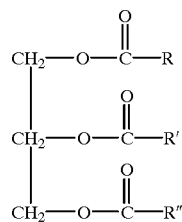

where R, R' and R" may be the same or different fatty acid radicals. Examples of suitable naturally-occurring fats and oils include, but are not limited to, the following compounds: *Adansonla Digitata* Oil; Apricot (*Prunus Armeniaca*) Kernel Oil; *Argania Spinosa* Oil; *Argemone Mexicana* Oil; Avocado (*Persea Gratissima*) Oil; Babassu (*Orbignya Olelfera*) Oil; Balm Mint (*Melissa Officinalis*) Seed Oil; Bitter Almond (*Prunus Amygdalus Amara*) Oil; Bitter Cherry (*Prunus Cerasus*) Oil; Black Currant (*Ribes Nigrum*) Oil; Borage (*Borago Officinalis*) Seed Oil; Brazil (*Bertholletia Excelsa*) Nut Oil; Burdock (*Arctium Lappa*) Seed Oil; Butter; C12–18 Acid Triglyceride; *Calophyllum Tacamahaca* Oil; *Camellia Kissi* Oil; *Camellia Oleifera* Seed Oil; Canola Oil; Caprylic/Capric/Liuric Triglyceride; Caprylic/Capric/Linoleic Triglyceride; Caprylic/Capric/Myristic/Stearic Triglyceride; Caprylic/Capric/Stearic Triglyceride; Caprylic/Capric Triglyceride; Caraway (*Carum Carvi*) Seed Oil; Carrot (*Daucus Carota Sativa*) Oil; Cashew (*Anacardium Occidentale*) Nut Oil; Castor Oil Benzoate; Castor (*Ricinus Communis*) Oil; Cephalins; Chaulmoogra (*Taraktogenos Kurzii*) Oil, Chia (*Salvia Hispanica*) Oil; Cocoa (*Theobrama Cocao*) Butter; Coconut (*Cocos Nucifera*) Oil; Cod Liver Oil; Coffee (*Coffea Arabica*) Oil; Corn (*Zea Mays*) Germ Oil; Corn (*Zea Mays*) Oil; Cottonseed (*Gossypium*) Oil; C10–18 Triglycerides; Cucumber (*Cucumis Sativus*) Oil; Dog Rose (*Rosa Canina*) Hips Oil; Egg Oil; Emu Oil; Epoxidized Soybean Oil; Evening Primrose (*Oenothera Biennis*) Oil; Fish Liver Oil; *Gevuina Avellana* Oil; Glyceryl Triacetyl Hydroxystearate; Glyceryl Triacetyl Ricinoleate; Glycolipids; Glycosphingolipids; Goat Butter; Grape (*Vitis Vinifera*) Seed Oil; Hazel (*Croylus Americana*) Nut Oil; Hazel (*Corylus Aveilana*) Nut Oil; Human Placental Lipids; Hybrid Safflower (*Carthamus Tinctorius*) Oil; Hybrid Sunflower (*Helianthus Annuus*) Seed Oil; Hydrogenated Canola Oil; Hydrogenated Castor Oil; Hydrogenated Castor Oil Laurate; Hydrogenated Castor Oil Triisosteareate; Hydrogenated Coconut Oil; Hydrogenated Cottonseed Oil; Hydrogenated C12–18 Triglycerides; Hydrogenated Fish Oil; Hydrogenated Lard; Hydrogenated Menhaden Oil; Hydrogenated Milk Lipids; Hydrogenated Mink Oil; Hydrogenated Olive Oil; Hydrogenated Orange Roughy Oil; Hydrogenated Palm Kernel Oil; Hydrogenated Palm Oil; Hydrogenated Peanut Oil; Hydrogenated Rapeseed Oil; Hydrogenated Shark Liver Oil; Hydrogenated Soybean Oil; Hydrogenated Tallow; Hydrogenated Vegetable Oil; Isatis Tinctoria Oil; Job's Tears (*Coix Lacryma-Jobi*) Oil; Jojoba Oil; Kiwi (*Actinidia Chinensis*) Seed Oil; Kukui (*Aleurites Moluccana*) Nut Oil; Lard; Lauric/Palmitic/Oleic Triglyceride; Linseed (*Linum Usitatissiumum*) Oil; Lupin (*Lupinus Albus*) Oil; *Macadamia* Nut Oil; *Macadamia Ternifolia* Seed Oil; *Macadamia Integrifolia* Seed Oil; Maleated Soybean Oil; Mango (*Mangifera Indica*) Seed Oil; Marmot Oil; Meadowfoam (*Limnanthes fragraAlba*) Seed Oil; Menhaden Oil; Milk Lipids; Mink Oil; *Moringa* Pterygosperma Oil; *Mortierella* Oil; Musk Rose (*Rosa Moschata*) Seed Oil; Neatsfoot Oil; Neem (*Melia Azadirachta*) Seed Oil; Oat (*Avena Sativa*) Kernel Oil; Oleic/Linoleic Triglyceride; Oleic/Palmitic/Lauric/Myristic/Linoleic Triglyceride; Oleostearine; Olive (*Olea Europaea*) Husk Oil; Olive (*Olea Europaea*) Oil; Omental Lipdis; Orange Roughy Oil; Ostrich Oil; Oxidized Corn Oil; Palm (*Elaeis Guineensis*) Kernel Oil; Palm (*Elaeis Guineensis*) Oil; Passionflower (*Passiflora Edulis*) Oil; Peach (*Prunus Persica*) Kernel Oil; Peanut (*Arachis Hypogaea*) Oil; Pecan (*Caiya Illinoensis*) Oil; Pengawar Djambi (*Cibotium Barometz*) Oil; Phospholipids; Pistachio (*Pistacia Vera*) Nut Oil; Placental Lipids; Poppy (*Papaver Orientale*) Oil; Pumpkin (*Cucurbita Pepo*) Seed Oil; Quinoa (*Chenopodium Quinoa*) Oil; Rapeseed (*Brassica Campestris*) Oil; Rice (*Oryza Sativa*) Bran Oil; Rice (*Oryza Sativa*) Germ Oil; Safflower (*Carthamus Tinctorius*) Oil; Salmon Oil; Sandalwood (*Santalum Album*) Seed Oil; Seabuchthorn (*Hippophae Rhamnoides*) Oil; Sesame (*Sesamum Indicum*) Oil; Shark Liver Oil; Shea Butter (*Butyrospermum Parkii*); Silk Worm Lipids; Skin Lipids; Soybean (*Glycine Soja*) Oil; Soybean Lipid; Sphingolipids; Sunflower (*Helianthus Annuus*) Seed Oil; Sweet Almond (*Prunus Amygdalus Dulcis*) Oil; Sweet Cherry (*Prunus Avium*) Pit Oil; Tali Oil; Tallow; Tea Tree (*Melaleuca Alternifolia*) Oil; *Telphairia Pedata* Oil; Tomato (*Solanum*

*Lycopersicum*) Oil; Triarachidin; Tiibehenin; Tricaprin; Tricaprylin; *Trichodesma Zeylanicum* Oil; Trierucin; Triheptanoin; Triheptylundecanoin; Trihydroxymethoxystearin; Trihydroxystearin; Triisononanoin; Triisopalmitin; Triisostearin; Trilaurin; Trilinolein; Trilinolenin; Trimyristin; Trioctanoin; Triolein; Tripalmitin; Tripalmitolein; Triricinolein; Trisebacin; Tristearin; Triundecanoin; Tuna Oil; Vegetable Oil; Walnut (*Juglans Regia*) Oil; Wheat Bran Lipids; and Wheat (*Triticum Vulgare*) Germ Oil.

The amount of gelling agent used in preparing the gelled ester compositions, the gelled ether compositions, the gelled alcohol compositions, or the gelled naturally-occurring fat and oil compositions may range from about 0.2% to about 80% by weight, depending on the desired properties of the resulting gelled component. Preferably, a gelling agent is present in the gelled ester compositions, the gelled ether compositions, the gelled alcohol compositions, or the gelled naturally-occurring fat and oil compositions from about 1% to about 40% by weight. More preferably, a gelling agent is present in the gelled ester compositions, the gelled ether compositions, the gelled alcohol compositions, or the gelled naturally-occurring fat and oil compositions from about 5% to about 30% by weight. In embodiments where both a diblock copolymer and a triblock copolymer are used, the triblock copolymer may range from about 0.1% to about 30% by weight and the diblock copolymer from about 1% to about 40% by weight.

It is noted that the gelled ester compositions, the gelled ether compositions, the gelled alcohol compositions, and the gelled naturally-occurring fat and oil compositions may optionally include one or more additional components. The additional component maybe a suspended component and/or an active ingredient.

Examples of suitable solids which can be suspended in the gelled ester, gelled ether, gelled alcohol, and gelled naturally-occurring fat and oil compositions include, but are not limited to, zinc oxide, coated zinc oxide, surface-treated zinc oxide, titanium dioxide, coated titanium dioxide, surface-treated titanium dioxide, phosphorescent substances, fluorescent materials, molybdenum oxide, zinc sulfide, copper-doped zinc sulfide, graphite, explosive materials, pesticides, herbicides, fungicides, insecticides, plasticizers, air sensitive chemicals, moisture sensitive chemicals, boron nitride, iron oxides, talc, mica, plastics, polymers, silica, silicon dioxide, aluminum oxide, organic materials, inorganic materials, organometallic materials, metal particles, medical materials (such as antibacterials, antibiotics, antimicrobials, antifungals, and anesthetics), glass, clays, gums, capsules containing am active ingredient, starch, modified starch, fragrances, color pigments, sunscreen active particles, glitters, other encapsulated materials, and combinations thereof.

Examples of suitable liquids which can be suspended in the gelled ester, gelled ether, gelled alcohol, and gelled naturally-occurring fat and oil compositions include, but are not limited to water, water containing one or more water soluble materials, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and combinations thereof.

Examples of suitable gases which can be suspended in the gelled ester, gelled ether, gelled alcohol, and gelled naturally-occurring fat and oil compositions include, but are not limited to, hydrogen, chloride, air, nitrogen, oxygen, carbon dioxide, propane, neon, helium, and combinations thereof.

The second component used in forming the two-phase gel composition is a hydrocarbon-based solvent. Preferably, a suitable solvent should be hydrophobic and non-polar. The solvent is generally water insoluble, has a relatively low viscosity, and is substantially free of polymer. The selection of the solvent for use in the two-phase gel composition depends on a variety of factors such as the desired properties of the two-phase gel composition such as the viscosity, the desired properties of the end product in which the two-phase gel composition may be incorporated such as the viscosity, the processing temperature, the mixing capabilities, the desirability of raw materials, and the like.

The solvents suitable for use in the two-phase gel composition include, but are not limited to, any compounds which are hydrophobic and non-polar. Examples of suitable solvents for use in the two-phase gel composition include, but are not limited to, oils, mineral white oils, solvents, base oils, technical mineral oils, synthetic hydrocarbons, solid hydrocarbons, semi-solid hydrocarbons, waxes, petroleum distillates, petrolatums, and combinations thereof. In some embodiments, the solvent maybe a paraffinic or a naphthenic oil. Although the solvent for use in the two-phase gel composition may be in the form of a semi-solid or solid, it is preferably in the form of a liquid for ease of handling.

Examples of suitable commercially available hydrophobic, non-polar solvents include, but are not limited to Excel® 260-HC which is available from Excel Paralubes; Isopar® L, Isopar® M, and Isopar® V which are available from Exxon Chemical; Drakeol® 7, Drakeol® 31, Drakeol® 34, Snow White Petrolatum, and Amber Petrolatum which are available from Penreco; Conosol® C145, Conosol® 200, Conosol® 260, and Conosol® V 340 which are available from Conoco, Inc.; Permethyl® 99A, Permethyl® 101A, and Permethyl® 102A which are available from Presperse; and Panalane® L14E which is available from Amoco.

The amount of the hydrophobic, non-polar solvent for use in the two-phase gel composition depends on a variety of factors such as the desired properties of the two-phase gel composition such as the viscosity, the desired properties of the end product in which the two-phase gel composition may be incorporated such as the viscosity, the processing temperature, the mixing capabilities, and the like. In some embodiments, the amount of the solvent component present in the two-phase gel composition may range from about 5% to about 95% by weight of the two-phase gel composition. In certain other embodiments, the solvent component is present in an amount from about 40% to about 95% by weight of the two-phase gel composition. In still other embodiments, the solvent component is present in an amount from about 60% to about 90% by weight of the two-phase gel composition. In yet other embodiments, the solvent component is present in an amount from about 60% to about 80% by weight of the two-phase gel composition.

The gelled ester compositions, gelled ether compositions, gelled alcohol compositions, and gelled naturally-occurring fat and oil compositions used in making the two-phase gel compositions may be obtained by the methods described in U.S. application Ser. No. 09/419,571 filed on Oct. 18, 1999, which is incorporated herein by reference. First, one or more esters, ethers, alcohols, or naturally-occurring fat and oil compounds to be gelled are mixed with a gelling agent. Second, the mixture typically is heated to a temperature in the range of about 70° C. to about 140° C., although other temperatures also are acceptable. The mixture is agitated until a homogeneous mixture is obtained. The homogeneous mixture is then cooled to room temperature to form a gelled ester composition, a gelled ether composition, a gelled alcohol composition, or a gelled naturally-occurring fat and oil composition. It is noted that the compound to be gelled need not be mixed with a gelling agent before heating. Instead, the compound may be heated to a desired temperature first and then the gelling agent may be added to the compound.

The two-phase gel compositions maybe obtained by various methods. The methods of preparing the two-phase gel compositions described herein are advantageous in that they require only slightly elevated processing temperatures and generally short mixing times. The two-phase gel compositions obtained by the methods described herein have a viscosity which is greater than or equal to the viscosity of the first component (i.e., the gelled ester composition, gelled ether composition, gelled alcohol composition, gelled naturally-occurring fat and oil composition, or a combination thereof), the second component (the solvent), and the sum of the viscosity of the first and second components. In some embodiments, the two-phase gel compositions obtained by the methods described herein possess a viscosity which is slightly greater than or equal to the viscosity of the first component, the second component, and/or the sum of the first and second components. In other embodiments, the two-phase gel compositions obtained by the methods described herein have a viscosity which is substantially greater than the sum of the viscosity of each component.

In accordance with embodiments of the invention, a two-phase gel composition may be obtained by the following method. First, one or more of the gelled ester, gelled ether, gelled alcohol, or gelled naturally-occurring fat and oil compositions are mixed with one or more hydrophobic, non-polar solvents to form a mixture. Second, the mixture is heated typically to a temperature in the range of about 40° C. to about 60° C., although other temperatures also are acceptable. The mixture is then agitated until a homogenous mixture is obtained. The homogenous mixture is then cooled to room temperature. A two-phase gel composition is thus obtained.

In accordance with other embodiments, a two-phase gel composition may be obtained by the following method. First, one or more gelled ester, gelled ether, gelled alcohol, or gelled naturally-occurring fat and oil compositions are heated to a temperature typically in the range of about 40° C. to about 60° C., although other temperatures are also acceptable. Second, the heated gelled component is mixed with one or more hydrophobic, non-polar solvents. The mixture is agitated until a homogenous mixture is obtained. The homogenous mixture is then cooled to room temperature. A two-phase gel composition is thus obtained.

In accordance with further embodiments, a two-phase gel composition may be obtained by the following method. First, one or more hydrophobic, non-polar solvents are heated to a temperature typically in the range of about 40° C. to about 60° C., although other temperatures also are acceptable. Second, the heated solvent is mixed with one or more gelled ester, gelled ether, gelled alcohol, or gelled naturally-occurring fat and oil compositions to form a mixture. The mixture is then agitated until a homogeneous mixture is obtained. The homogeneous mixture is then cooled to room temperature. A two-phase gel composition is thus obtained.

In another embodiment, a two-phase gel composition may be obtained by the following method. First, one or more hydrophobic, non-polar solvents are heated to a temperature in the range of about 40° C. to about 60° C., although other temperatures also are acceptable. Separately, one or more gelled ester, gelled ether, gelled alcohol, or gelled naturally-occurring fat and oil compositions is heated to a temperature typically in the range of about 40° C. to about 60° C., although other temperatures also are acceptable. The heated solvent is then mixed with the heated gelled component to form a mixture. The mixture is then agitated until a homogenous mixture is obtained. The homogeneous mixture is then cooled to room temperature. A two-phase gel composition is thus obtained.

In yet another aspect, a two-phase gel composition may be obtained by the following method. The method involves mixing one or more gelled ester, gelled ether, gelled alcohol, or gelled naturally-occurring fat and oil compositions with one or more hydrophobic, non-polar solvents at room temperature to form a two-phase gel composition. In some embodiments, the two-phase gel composition obtained by this method may be used for spill control.

The following examples are given to illustrate embodiments of the invention. They are merely exemplary and are not intended to limit the scope of the invention otherwise described herein. All numerical values disclosed herein are approximate numbers. In some examples, an antioxidant was added in an amount of about 0.02%. In other examples, an antioxidant was added in an amount of about 0.05% to about 0.20%. Any antioxidant can be used. One suitable antioxidant is 2,6-di-tert-butyl-4-methylphenol ("BHT").

EXAMPLE 1

A sample of gelled isopropyl myristate (available under the trade name of Estol® IPM 1512 available from Unichema, Lexol® IPM available from Inolex, etc.) was prepared (85.28 wt. % isopropyl myristate+14.30 wt. % Kraton® G1702+0.40 wt. % Kraton® G1650). The finished gel exhibited excellent clarity and had a Brookfield viscosity (5 rpm, spindle T-C) of 157,000 cPs at 25° C.

EXAMPLE 2

A sample of gelled octyl methoxycinnamate (available under the trade names of Parsol® MCX available from Givaudan-Roure, Escalol® 557 available from ISP Van Dyk, TNeo Heliopan® AV available from Haarman & Reimer) was prepared (87.58 wt. % octyl methoxycinnamate+12.00 wt. % Kraton® G1701+0.40 wt. % Kraton® G1650). The finished gel was clear and stable through several freeze/thaw cycles.

EXAMPLE 3

A sample of zinc oxide suspension in gelled octyl methoxycinnamate was prepared by using 50.00 wt. % of zinc oxide and 50.00 wt. % of the gelled octyl methoxycinnamate illustrated in Example 2. The finished suspension had good consistency and maintained stability without separation for 15 days under thermal stress.

EXAMPLE 4

A sample of gelled propylene glycol dicaprylate/caprate (available under the trade name of Estol® PDCC1526 available from Unichema) was prepared (87.58 wt. % propylene glycol dicaprylate/caprate+12.00 wt. % Kraton® G1780+0.40 wt. % Kraton® G1650). The gel was clear at ambient temperature.

EXAMPLE 5

A sample of gelled isostearyl neopentanoate (available under the trade name of Dermol® 185 available from Bemel) was prepared (85.58 wt. % isostearyl neopentanoate+14.00 wt. % Septon® 1001+0.40 wt. % Kratong G1650). The finished gel was clear and stable without syneresis.

EXAMPLE 6

Jojoba oil gel was prepared (91.28 wt. % jojoba oil+0.4 wt. % Kraton® G1650+8.3 wt. % Kraton® G1702). The gel was clear and viscous.

EXAMPLE 7

Eicosyl erucate (available under the trade name of Erucical® EG-20 available from Lambent) gel was prepared (91.28 wt. % Erucical® EG-20+0.4 wt. % Kraton® G1650+ 8.3 wt. % Kraton® G1702). The gel was clear and stable without syneresis.

In addition to the above examples of gel compositions, various other gel compositions also were obtained. Tables 3–6 summarize the gel compositions obtained in accordance with embodiments of the invention.

TABLE 3

| INCI Name | Ester (wt. %) | Kraton® G1650 | Kraton® G1702 | Kraton® G1701 | Kraton® G1780 | Septon® 1001 | Kraton® FG1901 | Kraton® G1652 |
|---|---|---|---|---|---|---|---|---|
| Isopropyl Myristate | 85.28 | 0.4 | 14.3 | | | | | |
| | 90.58 | 0.4 | 9.00 | | | | | |
| Isopropyl Palmitate | 87.53 | 0.4 | 12.00 | | | | | |
| | 89.58 | 0.4 | 10.00 | | | | | |
| | 85.58 | 0.4 | 14.00 | | | | | |
| C12–15 Alkyl Benzoate | 83.58 | 0.4 | 16.00 | | | | | |
| | 87.58 | 0.4 | 12.00 | | | | | |
| | 87.98 | | 12.00 | | | | | |
| | 89.58 | 0.4 | 10.00 | | | | | |
| | 89.98 | 10.00 | | | | | | |
| Octyl Methoxycinnamate | 89.58 | 0.40 | 10.00 | | | | | |
| | 83.58 | 0.40 | 16.00 | | | | | |
| | 85.58 | 0.40 | 14.00 | | | | | |
| | 81.58 | 0.40 | 12.00 | | | | | |
| | 83.58 | 0.40 | | 16.00 | | | | |
| | 87.58 | 0.40 | | 12.00 | | | | |
| | 85.58 | 0.40 | | 14.00 | | | | |
| | 89.58 | 0.40 | | 10.00 | | | | |
| Octyl Dodecyl Neopentanoate | 81.98 | | | | 12.00 | | | |
| Isostearyl Neopentanoate | 85.58 | 0.40 | | | | | 14.00 | |
| | 81.98 | | | | 12.00 | | | |
| Tridecyl Salicylate | 87.58 | 0.40 | 12.00 | | | | | |
| | 91.28 | 0.4 | 8.30 | | | | | |
| Octyl Dodecanol | 89.58 | 0.4 | | 10.00 | | | | |
| | 88.89 | | | 6.67 | | | 4.44 | |
| | 90.00 | | 5.48 | | | | 4.5 | |
| | 90.00 | | 5.45 | | | | | 4.5 |
| | 87.58 | 0.4 | 12.00 | | | | | |
| | 89.58 | 0.4 | 10.00 | | | | | |
| Propylene Glycol Dicaprylate/caprate | 87.58 | 0.4 | | | 12.00 | | | |
| Jojoba Oil | 91.28 | 0.4 | 8.30 | | | | | |

TABLE 4

| | Polymer Type | Ester (%) | Polymer (%) | Antioxidant (%) |
|---|---|---|---|---|
| 1,2-benzene-dicarboxylic acid, di-C$_{8-10}$ br alkyl ester | Vector® 6030 | 91.98 | 8 | 0.02 |
| | Vector® 8550 | 91.98 | 8 | 0.02 |
| | Vector® 2518P | 91.98 | 8 | 0.02 |
| | Solprene® S200 | 91.98 | 8 | 0.02 |
| 1,2 benzene-dicarboxylic acid, di-undecyl ester | Vector® 6030 | 91.98 | 8 | 0.02 |

TABLE 5

| Oil Type | Polymer Type | Oil(%) | Polymer (%) | Antioxidant (%) |
|---|---|---|---|---|
| Sunflower Seed Oil | Kraton® D1102 | 91.9 | 8 | 0.10 |
| | Kraton® D1133 | 91.9 | 8 | 0.10 |
| | Kraton® D1101 | 91.9 | 8 | 0.10 |
| | Vector® 6030 | 91.9 | 8 | 0.10 |
| Corn Oil | Vector® 6030 | 91.9 | 8 | 0.10 |
| Sesame Oil | Vector® 6030 | 91.9 | 8 | 0.10 |
| Soybean Oil | Kraton® D1101 | 89.90 | 10 | 0.10 |
| | Kraton® D1102 | 85.98 | 14 | 0.02 |
| | Vector® 6030 | 91.90 | 8 | 0.10 |
| Linseed Oil | Kraton® D1102 | 85.90 | 14 | 0.10 |
| | Vector® 6030 | 91.90 | 8 | 0.10 |

TABLE 6

| Oil Type | Oil (%) | Isopropyl Palmitate (%) | Alkyl Galactomannan (%) | Antioxidant (%) |
|---|---|---|---|---|
| Sunflower Seed Oil | 46.99 | 46.99 | 6.0 | 0.02 |
| | 44.99 | 44.99 | 10.0 | 0.02 |
| | 75.18 | 18.8 | 6.0 | 0.02 |
| | 71.95 | 18.0 | 10.0 | 0.05 |
| Corn Oil | 75.1 | 18.8 | 6.0 | 0.10 |
| | 71.9 | 18.0 | 10.0 | 0.10 |
| Soybean Oil | 75.1 | 18.8 | 6.0 | 0.10 |
| | 71.9 | 18.0 | 10.0 | 0.10 |
| Sesame Oil | 68.9 | 25.0 | 6.0 | 0.10 |
| | 65.31 | 25.5 | 9.1 | 0.09 |
| Olive Oil | 68.9 | 25.0 | 6.0 | 0.10 |
| | 65.9 | 25.0 | 9.0 | 0.10 |

EXAMPLE 8

A sample of gelled soybean oil (available under the trade name of Alkali Refined Soybean Oil from Cargill) was prepared (85.90 wt. % soybean oil+14.00 wt. % Kraton® D1102). The finished gel exhibited excellent clarity and had a Brookfield viscosity (2.5 rpm, spindle T-C) of 18,000 cPs at 22° C. The gel was clear and remained clear and stable after being tested for accelerated aging in an oven at 50° C. for four weeks and three freeze/thaw cycles (−20° C. to 25° C.). The gelled soybean oil was then mixed with a hydrocarbon solvent, Conosol® 340, in the weight ratios set forth in Table 7 at 40–45° C. for 15–20 min to form five two-phase gel compositions, Two-Phase Gel Compositions 1–5.

TABLE 7

| Component | Two-Phase Gel Composition 1 | Two-Phase Gel Composition 2 | Two-Phase Gel Composition 3 | Two-Phase Gel Composition 4 | Two-Phase Gel Composition 5 |
|---|---|---|---|---|---|
| Gelled Soybean Oil (wt. %) | 20 | 30 | 40 | 50 | 70 |
| Conosol ® 340 (wt. %) | 80 | 70 | 60 | 50 | 30 |

Tables 8 and 9 provide information about the physical and chemical properties of Conosol® 340 available from Conoco, Inc.

TABLE 8

| Property | Specification | Typical | Test Method |
|---|---|---|---|
| API Gravity, 15.6° C. (60° F.) | 31.0–34.0 | 32 | ASTM D-287 |
| Specific Gravity, 15.6° C. (60° F.) | | 0.8654 | Calculated |
| Pounds per Gallon, 15.6° C. (60° F.) | | 7.22 | Calculated |
| Refractive Index, 20° C. (68° F.) | | 1.4714 | ASTM-D1218 |
| Flash Point, Closed Cup, ° C., (° F.) | 171 (340) Min. | 177 (350) | ASTM D-93 |
| Pour Point, ° C., (° F.) | | −45 (−50) | ASTM D-97 |
| Kauri-Butanol No. | | 22.4 | ASTM D-1133 |
| Aniline Point, ° C., (° F.) | | 90 (195) | ASTM D-611 |
| Color, Saybolt | | +27 | ASTM D-156 |
| Sulfur, PPM | | <1 | ASTM D-4045 |
| Composition, Wt. % | | | SFC, Pennzoil Method |
| Saturates | | >99.5 | |
| Aromatics | | <0.5 | |
| Viscosity @ 40 C., cSt (SUS) | | 10.2 (59.5) | ASTM D-445 |
| Distillation Range | | | ASTM D-86 |

TABLE 9

| | ° C. | ° F. | Specification |
|---|---|---|---|
| I.B.P. | 327 | 620 | 316 (600) Min. |
| 5% | 332 | 630 | |
| 10% | 332 | 630 | |
| 50% | 335 | 635 | |
| 90% | 340 | 645 | |
| 95% | 342 | 648 | |
| E.P. | 349 | 660 | 360 (680) Max. |

FIG. 1 is a graph of viscosity versus gelled soybean oil concentration for Two-Phase Gel Compositions 1–5. The values of the Brookfield viscosity (2.5 rpm, spindle T-C at 22° C.) measurements and the concentrations of the gelled soybean oil component are shown in Table 10.

TABLE 10

| Gelled Soybean Oil Concentration (wt. %) | Viscosity (cPs) |
|---|---|
| 20 | 200,000 |
| 30 | 288,000 |
| 40 | 180,000 |
| 50 | 40,000 |
| 70 | 17,000 |
| 100 | 18,000 |

Two-Phase Gel Compositions 1–5 were clear and showed excellent thermal stability after two weeks in an oven at 50° C. and three freeze/thaw cycles.

EXAMPLE 9

A sample of gelled soybean oil (available under the trade name of Alkali Refined Soybean Oil from Cargill) was prepared (85.90 wt. % soybean oil+14.00 wt. % Kraton® D1102). The finished gel exhibited excellent clarity and had a Brookfield viscosity (50 rpm, spindle T-C) of 18,000 cPs at 22° C. The gel was clear and remained clear and stable after being tested for accelerated aging in an oven at 50° C. for four weeks and three freeze/thaw cycles (−20° C. to 25° C.).

The gelled soybean oil was then mixed with a hydrocarbon solvent, a low sulfur content diesel fuel available from Amoco, in the weight ratios set forth in Table 11 below at room temperature for 15–20 min to form three two-phase gel compositions, Two-Phase Gel Compositions 6–8.

TABLE 11

| Component | Two-Phase Gel Composition 6 | Two-Phase Gel Composition 7 | Two-Phase Gel Composition 8 |
| --- | --- | --- | --- |
| Gelled Soybean Oil (wt. %) | 90 | 80 | 65 |
| Diesel Fuel (wt. %) | 10 | 20 | 35 |

Figure 2:
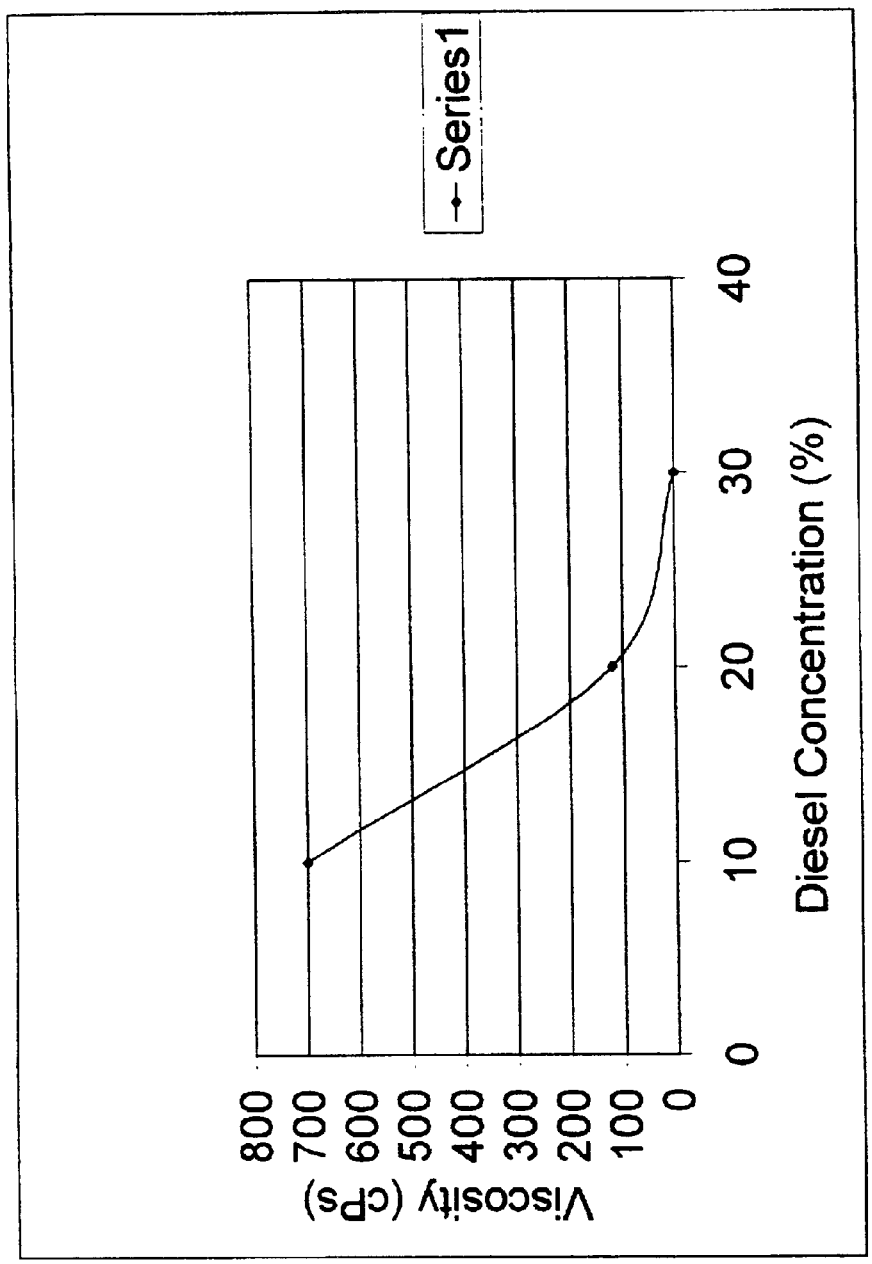
FIG. 2 is a graph of viscosity versus concentration for a two-phase gel composition according to another embodiment of the invention.

FIG. 2 is a graph of viscosity versus diesel fuel concentration for Two-Phase Gel Compositions 6–8. The values of the Brookfield viscosity (50 rpm, spindle T-C at 22° C.) measurements and the concentrations of the diesel fuel component are shown in Table 12.

TABLE 12

| Diesel Fuel Concentration (wt. %) | Viscosity (cPs) |
| --- | --- |
| 10 | 700 |
| 20 | 120 |
| 35 | 0 |

Two-Phase Gel Compositions 6–8 were stable for 3 months at room temperature.

EXAMPLE 10

A sample of gelled soybean oil (available under the trade name of Alkali Refined Soybean Oil from Cargill) was prepared (87.80 wt. % soybean oil+12.00 wt. % Kraton® D1160). The finished gel exhibited excellent clarity and had a Brookfield viscosity (2.5 rpm, spindle T-C) of 5,000 cPs at 25° C.

The gelled soybean oil was mixed with mineral oil (available under the trade name of Excel® 260-HC) (35 wt. % gelled soybean oil+65 wt. % Excel® 260-HC) to form a two-phase gel composition. Table 13 provides information about the physical and chemical properties of Excel® 260-HC available from Excel Paralubes.

TABLE 13

Physical and Chemical Properties

Appearance: Clear and bright
Odor: Hydrocarbon
Physical state: No information available
pH: No data available
Boiling Point: 707–964.9 F., 375–518.3 C.
Melting Point: Not applicable
Specific Gravity: 0.87
Pour Point: 5° F., −15° C.
Vapor Pressure: <1 mm Hg @ 392° F.
Vapor Density (air = 1): >1
Percent Volatile by Volume: No data available
Volatile Organic Content: No data available
Molecular Weight: >350
Average Carbon Number: No data available
Viscosity @ 100° F.: 259 SUS
Viscosity @ 40° C.: 50.1 cSt
Solubility in Water: Insoluble in water
Octanol/Water Coefficient: Log $K_{ow}$ = No data available The two-phase gel composition had a Brookfield viscosity (2.5 rpm, spindle T-C) approximately 1000 times greater than the original gelled soybean oil. The two-phase gel composition exhibited excellent thermal stability and clarity.

EXAMPLE 11

A sample of gelled isopropyl myristate (available under the trade name of Isopropyl Myristate from Spectrum) was prepared (74.95 wt. % isopropyl myristate+25.00 wt. % Kraton® D1102). The finished gel was opaque and had a Brookfield viscosity (5 rpm, spindle T-C) of 9,800 cPs at 25° C.

The gelled isopropyl myristate was mixed with Conosol® 340 (13 wt. % gelled isopropyl myristate+87 wt. % Conosol® 340) to form a two-phase gel composition. The two-phase gel composition had a Brookfield viscosity (2.5 rpm, spindle T-C) approximately 100 times greater than the original gelled isopropyl myristate. The two-phase gel composition was hazy at room temperature and had limited stability.

EXAMPLE 12

A sample of gelled isopropyl myristate (available under the trade name of Isopropyl Myristate from Spectrum) was prepared (85.95 wt. % isopropyl myristate+14.00 wt. % Kraton® G1650). The finished gel exhibited a water-white clarity and excellent stability and had a Brookfield viscosity (2.5 rpm, spindle T-C) of 3600 cPs at 25° C.

The gelled isopropyl myristate was mixed with Drakeol® 7 (30 wt. % gelled isopropyl myristate+70 wt. % Drakeol® 7) at 50° C. for 15 minutes to form a two-phase gel composition. Table 14 provides information about the physical and chemical properties of Drakeol® 7 available from Penreco.

TABLE 14

| Typical Values | | | | | Typical Properties | | | |
|---|---|---|---|---|---|---|---|---|
| Viscosity | | API | Specific Gravity | | Flash Point | | Pour Point | |
| ASTM D 445 | | | | | | | | |
| SUS @ | CST @ | ASTM D 1298 | | | ASTM D 92 | | ASTM D 97 | |
| 100° F. | 40° C. | @ 60° F. | @ 60° F. | @ 77° F. | ° F. | ° C. | ° F. | ° C. |
| 65/75 | 10.8/13.6 | 34.4/38.5 | .832/.853 | .826/.847 | 350 | 177 | 15 | −9 |

The two-phase gel composition had excellent clarity and thermal stability and had a Brookfield viscosity (2.5 rpm, spindle T-C) of 219,000 cPs at 25° C.

EXAMPLE 13

A sample of gelled isopropyl myristate (available under the trade name of Isopropyl Myristate from Spectrum) was prepared (73.95 wt. % isopropyl myristate+26.00 wt. % Kraton® G1650). The finished gel exhibited a water-white clarity and excellent stability and had a Brookfield viscosity (5 rpm, spindle T-C) of 117,000 cPs at 25° C.

The gelled isopropyl myristate was mixed with Excel® 260-HC and Isopar® M (28 wt. % gelled isopropyl myristate, 36 wt. % Excel® 260-HC, and 36 wt. % Isopar® M) to form a two-phase gel composition. Table 15 provides information about the physical and chemical properties of Isopar® M available from Exxon Chemical.

TABLE 15

| Property | Value |
|---|---|
| Solvency | |
| Kauri-butanol value | 25 |
| Aniline point, ° C. (° F.) | 91(196) |
| Volatlility | |
| Flash point, TCC, ° C. (° F.) | 93(199) |
| Distillation, ° C. (° F.) | |
| IBP | 223(433) |
| Dry point | 254(489) |
| Gravity | |
| specific @ 15.6° C. (60° F.) | 0.79 |
| Composition, mass % | |
| Saturates | 99.9 |
| Aromatics | <0.05 |

TABLE 15-continued

| Property | Value |
|---|---|
| Purity, ppm | |
| Acids | None |
| Clorides | — |
| Nitrogen | — |
| Peroxides | <1 |
| Sulfur | <2 |
| Surface properties | |
| Surface tension, dynes/cm @ 25° C. (77° F.) | 26.4 |
| Interracial tension with @ 25° C. (77° F.) | 52.2 |
| Demulsibility | Excellent |

The two-phase gel composition had a Brookfield viscosity (5 rpm, spindle T-C) approximately 1000 times greater than the original gelled isopropyl myristate. The two-phase gel composition had excellent clarity and thermal stability.

EXAMPLE 14

A sample of gelled isopropyl myristate (available under the trade name of Isopropyl Myristate from Spectrum) was prepared (79.95 wt. % isopropyl myristate+20.00 wt. % Kraton® G1650). The finished gel exhibited a water-white clarity and excellent stability and had a Brookfield viscosity (1 rpm, spindle T-E) of 12,000 cPs at 25° C.

The gelled isopropyl myristate was mixed with Excel® 260-HC in the weight ratios set forth in Table 16 to prepare six two-phase gel compositions, Two-Phase Gel Compositions 9–14:

TABLE 16

| Component | Two-Phase Gel Composition 9 | Two-Phase Gel Composition 10 | Two-Phase Gel Composition 11 | Two-Phase Gel Composition 12 | Two-Phase Gel Composition 13 | Two-Phase Gel Composition 14 |
|---|---|---|---|---|---|---|
| Gelled Isopropyl Myristate (wt. %) | 10 | 20 | 30 | 40 | 50 | 70 |
| Excel ® 260-HC (wt. %) | 90 | 80 | 70 | 60 | 50 | 30 |

Figure 3:
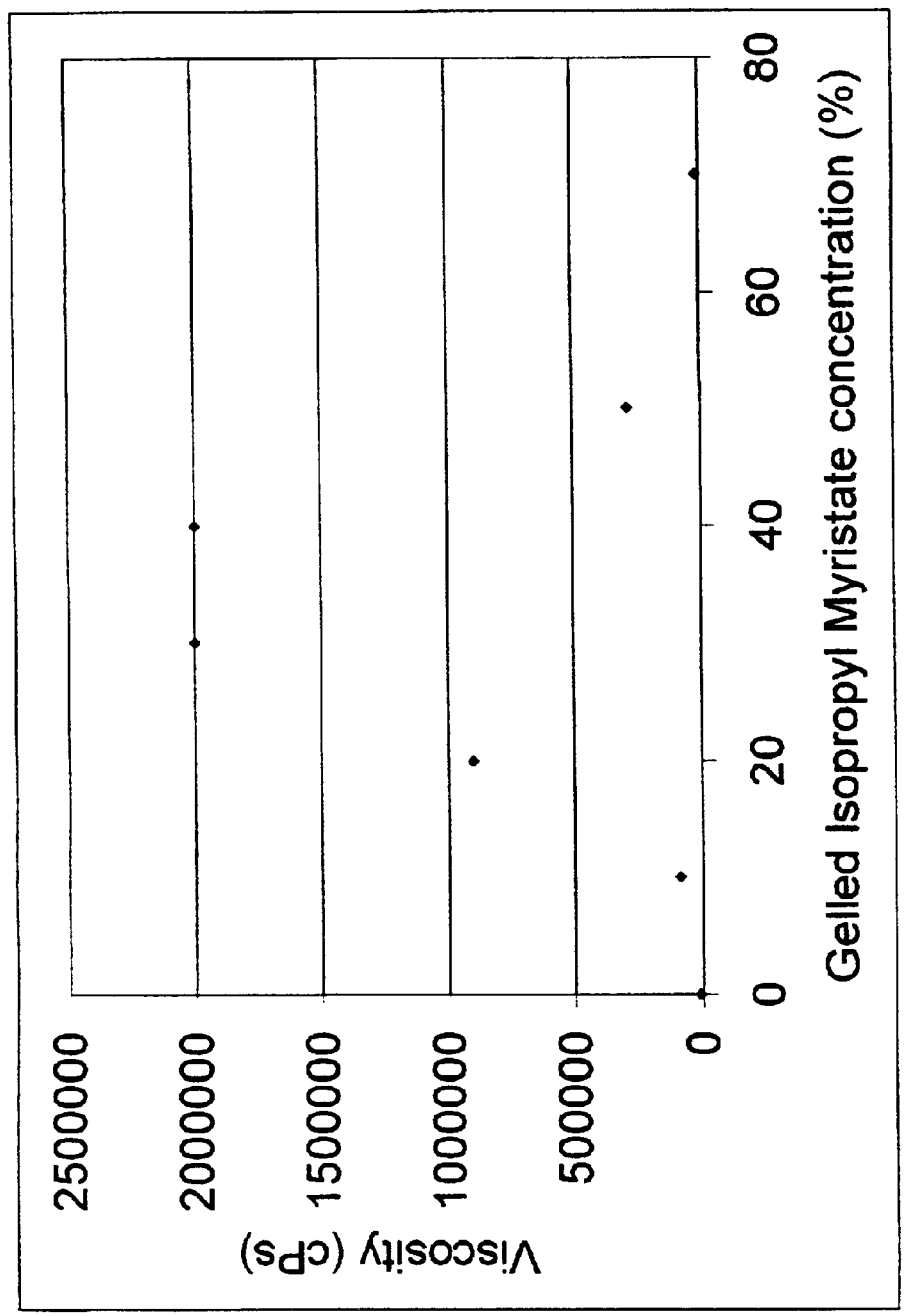
FIG. 3 is a graph of viscosity versus concentration for a two-phase gel composition according to another embodiment of the invention.

FIG. 3 is a graph of viscosity versus gelled isopropyl myristate concentration for Two-Phase Gel Compositions 9–14. The values of the Brookfield viscosity (1 rpm, spindle T-E at 25° C.) measurements and the concentrations of the gelled isopropyl myristate component are shown in Table 17.

TABLE 17

| Gelled Isopropyl Myristate Concentration (wt. %) | Viscosity (cPs) |
| --- | --- |
| 10 | 88,000 |
| 20 | 900,000 |
| 30 | 2,000,000 |
| 40 | 2,000,000 |
| 50 | 286,000 |
| 70 | 12,000 |

Two-Phase Gel Compositions 9–14 were clear and showed excellent thermal stability after two weeks in an oven at 50° C. and three freeze/thaw cycles.

EXAMPLE 15

A gelled blend of C12–15 Alkyl Benzoate (available under the trade name of Finsolv®TN from Finetex), Peanut Oil (available from Spectrum), and Kraton® D1102 was prepared. C12–15 Alkyl Benzoate was blended (42.9 wt. %) with the Peanut Oil (42.9 wt. %) and heated to 70–75° C. Kraton® D1102 was then added (14 wt. %) to form the gelled blend. The finished gelled blend had a slightly yellow color and excellent clarity and thermal stability. The finished gelled blend had a Brookfield viscosity (5 rpm, spindle T-C) of 4,800 cPs at 25° C.

The gelled blend was then mixed with Conosol® 260 (70 wt. % of the gelled blend and 30 wt. % Conosol® 260) to form a two-phase gel composition. The two-phase gel composition had excellent clarity and viscosity and a Brookfield viscosity (5 rpm, spindle T-C) of 5000 cPs at 25° C. Tables 18 and 19 provide information about the physical and chemical properties of Conosol® 260 available from Conoco, Inc.

TABLE 19

|  | ° C. | ° F. | Specification |
| --- | --- | --- | --- |
| I.B.P. | 271 | 520 | 260 (500) Min. |
| 5% | 280 | 536 |  |
| 10% | 281 | 537 |  |
| 50% | 291 | 555 |  |
| 90% | 309 | 589 |  |
| 95% | 313 | 596 |  |
| E.P. | 324 | 615 | 329 (625) Max. |

The two-phase gel compositions in accordance with embodiments of the invention have numerous cosmetic, health and beauty, home care, and industrial applications. The two-phase gel compositions may be used alone or in combination with one or more additional ingredients. The amount of the additional component used in the two-phase gel composition depends upon the desired properties of the end product in which the two-phase gel composition may be used. For example, the two-phase gel compositions are suitable as lubricants, suspending agents, emulsion stabilizers, thickening agents, personal care ingredients, air freshener components, pesticide and insecticide components, ingredients for candle and ornamental products, pharmaceutical carriers and carrier ingredients, ointment base ingredients, sporting good ingredients, ingredients for cleaning products, ingredients for explosives and explosive emulsions, spill control agents, ingredients for drilling mud, ingredients for well completion, and vehicles for carrying other materials. Since esters are generally considered biodegradable materials, this allows gelled esters to find application in products where minimal pollution is desired. Examples include fishing line lubricant, solder flux, agricultural dust reduction and lubrication, textile coating, protective coating for transporting fragile or environmentally-sensitive materials, and biodegradable oils and greases.

It has been discovered that the two-phase gel compositions in accordance with embodiments of the invention keep solids, liquids, and/or gases substantially uniformly suspended and evenly dispersed over a substantial period of

TABLE 18

| Property | Specification | Typical | Test Method |
| --- | --- | --- | --- |
| API Gravity, 15.6° C. (60° F.) | 37.0–40.0 | 38.5 | ASTM D-287 |
| Specific Gravity, 15.6° C. (60° F.) |  | 0.8324 | Calculated |
| Pounds per Gallon, 15.6° C. (60° F.) |  | 6.94 | Calculated |
| Refractive Index, 20° C. (68° F.) |  | 1.4571 | ASTM-D1218 |
| Flash Point, Closed Cup, ° C., (° F.) | 116 (240) Min. | 121 (250) | ASTM D-93 |
| Pour Point, ° C. (° F.) |  | −51 (−60) | ASTM D-97 |
| Kauri-Butanol No. |  | 23.8 | ASTM D-1133 |
| Aniline Point, ° C. (° F.) |  | 86 (187) | ASTM D-611 |
| Color, Saybolt |  | +30 | ASTM D-156 |
| Sulfur, PPM |  | <1 | ASTM D-4045 |
| Composition, Wt. % |  |  | SFC, Pennzoil Method |
| Saturates |  | >99.5 |  |
| Aromatics |  | <0.5 |  |
| Viscosity @ 40 C., cSt (SUS) |  | 4.3 (40.2) | ASTM D-445 |
| Distillation Range |  |  | ASTM D-86 | time. The suspended solids, liquids, and/or gases may be present in the two-phase gel compositions in amounts of up to about 95 wt. %. Suitable solids, liquids, and/or gases that can be suspended in the two-phase gel compositions include any solid, non-hydrocarbon liquid, or gas which will disperse into the gel and remain substantially suspended or evenly dispersed therein.

Examples of suitable solids which can be suspended in the two-phase gel compositions include, but are not limited to, zinc oxide, coated zinc oxide, surface-treated zinc oxide, titanium dioxide, coated titanium dioxide, surface-treated titanium dioxide, phosphorescent substances, fluorescent materials, molybdenum oxide, zinc sulfide, copper-doped zinc sulfide, graphite, explosive materials, pesticides, herbicides, fungicides, insecticides, plasticizers, air sensitive chemicals, moisture sensitive chemicals, boron nitride, iron oxides, talc, mica, plastics, polymers, silica, silicon dioxide, aluminum oxide, organic materials, inorganic materials, organometallic materials, metal particles, medical materials (such as antibacterials, antibiotics, antimicrobials, antifungals, and anesthetics), glass, clays, gums, capsules containing an active ingredient, starch, modified starch, fragrances, color pigments, sunscreen active particles, glitters, other encapsulated materials, and combinations thereof.

Examples of liquids which can be suspended in the two-phase gel compositions include, but are not limited to, water, water containing one or more water soluble materials, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and combinations thereof.

Examples of gases which can be suspended in the two-phase gel compositions include, but are not limited to, hydrogen, chloride, air, nitrogen, oxygen, carbon dioxide, propane, neon, helium, and combinations thereof Pending U.S. patent application Ser. No. 09/007,838, entitled "Hydrocarbon Gels as Suspending and the Dispersing Agents and Products," filed Jan. 15, 1998, discloses methods of making a suspension system based on gelled hydrocarbons. The disclosed methods can be utilized in embodiments of the invention to make suspension systems which are based on gelled esters, gelled ethers, gelled alcohols, or gelled naturally-occurring fats and oils. The disclosure of the above-referenced patent application is incorporated by reference in its entirety herein.

The two-phase gel compositions in accordance with embodiments of the invention also have a wide spectrum of cosmetic and health and beauty applications when the gel compositions include an effective amount of one or more cosmetic and health and beauty aid ingredients. By "effective amount," it is meant that a sufficient amount of the ingredient is present to be effective for the indicated purpose in the composition. An effective amount may range from about 0.001 to about 95 wt. %. By "cosmetic and health and beauty aid ingredients," it is meant any material which can be applied topically to the human skin or any part thereof for cleansing, beautifying, promoting attractiveness, and protecting or altering the appearance of the skin without altering or interfering with the physiological competence of the human skin or body. Included within this definition are creams, lotions, emollients, fragrance oils, massage oils, moisturizers, humectants, cosmetic oils, and so on. The two-phase gel compositions in accordance with embodiments of the invention also may contain skin care preservatives, diluents, surfactants, anti-wrinkle agents, and the like.

Furthermore, the two-phase gel compositions may be utilized to manufacture various over-the-counter ("OTC") products. An OTC product may be made entirely from a gel composition or only a component of the OTC is made from the gel composition. Examples of OTC products include, but are not limited to, antiperspirants, lip balms, and sunscreens (e.g., natural sunblocks, such as submicron particles of metal oxides or synthetic sunblock agents, such as octyl methoxycinnamate and benzophenone-3).

As mentioned above, the two-phase gel compositions in accordance with embodiments of the invention maybe utilized as carrier vehicles for topical administration of various cosmetic and health and beauty aid materials to the skin. Thus, such materials can be incorporated into the gel which are applied to the skin to be absorbed, to form a film on the skin, to provide a cooling sensation, to treat dry skin or oily skin, to work a material into the skin, to alter the overall texture of the skin, or to change color. All of these effects are sought to be achieved by various health and beauty aid products. Methods for making such skin care products are known in the art. For example, U.S. Pat. No. 5,558,872 discloses a clear gelled mineral oil based skin protectant. Similar skin protectants maybe made by substituting the mineral oil gel by the gel compositions in accordance with embodiments of the invention. The disclosure of U.S. Pat. No. 5,558,872 is incorporated by reference in its entirety herein.

It is noted that preferred uses of the two-phase gel compositions in accordance with embodiments of the invention include formation of thickened liquids, soft gels and semi-solid gels. Gels are particularly useful in waterproofing sunscreen compositions, makeup, mascara, etc. They also are useful in petrolatum-based products, such as petroleum jelly, makeup foundation, and night creams. They also can be used as substitutes for water-soluble polymers in products, such as lip rouge-cream, eyeliner liquid, and the like. They also may be used as a gelling agent in facial oil.

Semi-solid or solid gels have applications as toiletry sticks, such as a stick insect repellant or a matrix for clear or opaque stick products, which include deodorants, antiperspirants, lipsticks, analgesics, blushers, solid lotions and solid absorbable flexible gels. Methods for making such cosmetic sticks are known. For example, U.S. Pat. No. 5,756,082 discloses a cosmetic stick composition based on a hydrocarbon oil gel. The disclosed hydrocarbon oil gels may be substituted by the gel compositions in accordance with embodiments of the invention to make cosmetic stick compositions. The disclosure of U.S. Pat. No. 5,756,082 is incorporated by reference in its entirety herein.

The two-phase gel compositions in accordance with embodiments of the invention also have a wide spectrum of home care applications when the gel compositions include an effective amount of one or more home care ingredients. By "effective amount," it is meant that a sufficient amount of the ingredient is present to be effective for the indicated purpose in the composition. An effective amount may range from about 0.001 to about 95 wt. %. A "home care ingredient" may include, but is not limited to, any material which can be incorporated, blended and/or added to a hydrocarbon product for cleaning, refreshing, beautifying, etc. a home or the like. A "home care ingredient" may also include, but is not limited to, any material which can be used to protect and/or alter the appearance of a surface, i.e., by polishing or cleaning. Examples of home care applications include, but are not limited to, candles, air fresheners, aerosols, pesticides, herbicides, fungicides, plasticizers, insecticides, cleaning products, polishing products, and so on.

The two-phase gel compositions in accordance with embodiments of the invention also have a wide spectrum of industrial applications when the gel compositions include an effective amount of one or more industrial ingredients. For example, the two-phase gel compositions in accordance with embodiments of the invention may be utilized as carrier vehicles for fine particle industrial suspensions. Industrial applications may include a variety of both large and small-scale industrial applications. Examples of industrial applications include, but are not limited to, drilling mud and other fluids such as crude oil; drilling, formation, completion, and treatment of subterranean formations such as wells; cleaners; explosives; explosive emulsions; paint and coating applications; spill control; printing inks; brazing and soldering products; and so on. By "effective amount," it is meant that a sufficient amount of the ingredient is present to be effective for the indicated purpose in the composition. An effective amount may range from about 0.001 to about 95 wt. %.

As demonstrated above, the two-phase gel compositions in accordance with embodiments of the invention have a wide range of industrial, cosmetic, health and beauty, and home care applications. When so used, the two-phase gel compositions may exhibit one or more of the following properties or advantages: transparency; compatibility with active ingredients; reduction or elimination of syneresis; ability to act as a vehicle to provide a stable suspension of an ingredient such as an organic or inorganic material; moisturization; reduction in skin irritation; enhancement of wash-off resistance; provision of improved SPF when formulated into sunscreen products; reduction in absorption and irritation; rheology; control of rheology; solvency; wetting; elimination or minimization of whitening effect; ability to act as a moisture barrier; ability to act as a cosmetic base; controlled release of volatile or active ingredients; self-emulsifying; and formulation with less emulsifiers. Other properties and advantages are apparent to a person of ordinary skill in the art.

While the invention has been described with respect to a limited number of embodiments, modifications and variations therefrom exist. For example, although suitable esters, ethers, alcohols, and naturally-occurring fats and oils have been described with some depth, other compounds also can be used to form the gelled component. Additional suitable esters may include alkoxylated fatty acids, glyceryl ethers, and sorbitan derivatives. Additional suitable alcohols may include alkanolamides, alkanolamines, fatty alcohols, polyols, phenols, and sterols. Additional suitable ethers include heterocyclic ethers, e.g., tocopherol, alkoxylated alcohols, alkoxylated amides, alkoxylated amines, alkoxylated carboxylic acids, polymeric ethers, and glyceryl ethers. Similarly, naturally-occurring fats and oils may include so-called "essential oils," which are volatile organic constituents of plants normally obtained by distillation. In addition to the above-described compounds, aldehydes and ketones also may be formed into gel compositions in accordance with embodiments of the invention. In addition, although the two-phase gel composition is described as being made from the combination of a gelled ester, a gelled ether, a gelled alcohol, a gelled naturally-occurring fat and oil composition, or a combination thereof and a hydrophobic, non-polar solvent, other compounds can be used. For example, gelled aldehydes and gelled ketones also may be used to form the two-phase gel composition. The appended claims are intended to encompass all such modifications and the variations as falling within the scope of the invention.

What is claimed is:

1. A two-phase gel composition comprising:
   a gelled ester composition comprising a mixture of an ester compound and a polymer compound selected from the group consisting of triblock copolymers, star polymers, radial polymers, multi-block copolymers, and a combination thereof, the gelled ester composition having a viscosity $\eta_1$; and
   a hydrophobic, non polar solvent, the solvent having a viscosity $\eta_2$, wherein the two-phase gel composition is substantially free of phosphate compounds and has a viscosity $\eta$ which is greater than or equal to $\eta_1$ and which is greater than or equal to $\eta_2$.

2. The two-phase gel composition of claim 1, wherein the two-phase gel composition has a viscosity which is substantially greater than or equal to the sum of $\eta_1$ and $\eta_{22}$.

3. The two-phase gel composition of claim 1, further comprising a diblock copolymer, wherein the gelled ester composition is substantially free of mineral oils.

4. The two-phase gel composition of claim 1, wherein the ester compound is represented by the following formulas:

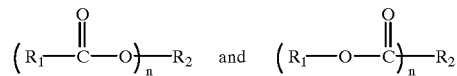

wherein n=1, 2, 3, and 4, and $R_1$ includes hydrogen, hydrocarbyl, phenyl, methoxyphenyl, alkylphenyl, substituted alkyl, or substituted phenyl; and
$R_2$ includes hydrogen, hydrocarbyl, phenyl, methoxyphenyl, alkylphenyl, substituted alkyl, substituted phenyl, alkylene, phenylene, substituted alkylene, or substituted phenylene.

5. The two-phase gel composition of claim 1, wherein the ester compound is represented by the following formula:

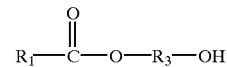

wherein $R_1$ includes hydrogen, hydrocarbyl, phenyl, methoxyphenyl, alkylphenyl, substituted alkyl, or substituted phenyl, and $R_3$ includes alkylene, phenylene, substituted alkylene, or substituted phenylene.

6. The two-phase gel composition of claim 1, wherein the ester compound is represented by the following formula:

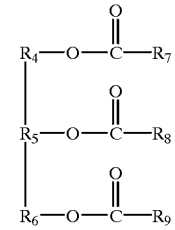

wherein $R_4$, $R_5$, and $R_6$ individually include alkylene, phenylene, substituted alkylene, or substituted phenylene, and $R_7$, $R_8$ and $R_9$ individually include hydrogen, hydrocarbyl, phenyl, methoxyphenyl, alkylphenyl, substituted alkyl, or substituted phenyl.

7. The two-phase gel composition of claim 1, wherein the ester compound is selected from the group consisting of isopropyl myristate, isopropyl palmitate, $C_{12}$–$C_{15}$ alkyl benzoate, octyl methoxycinnamate, octyl dodecyl neopentanoate, propylene glycol dicaprylate/caprate, jojoba oil, and isostearyl neopentanoate.

8. The two-phase gel composition of claim 3, wherein the diblock copolymer is selected from the group consisting of styrene-ethylene/propylene copolymers, styrene-ethylene/butadiene copolymers, styrene-isoprene copolymers, styrene-butadiene copolymers, and a mixture thereof.

9. The two-phase gel composition of claim 1, wherein the triblock copolymer is selected from the group consisting of styrene-ethylene/propylene-styrene copolymers, styrene-ethylene/butadiene-styrene copolymers, styrene-isoprene-styrene copolymers, styrene-butadiene-styrene copolymers, and a mixture thereof.

10. The two-phase gel composition of claim 1, wherein the solvent is selected from the group consisting of oils, mineral white oils, base oils, technical mineral oils, synthetic hydrocarbons, solid hydrocarbons, semi-solid hydrocarbons, waxes, petroleum distillates, petrolatums, and combinations thereof.

11. The two-phase gel composition of claim 1, wherein the gelled ester composition is present in the amount of about 5% to about 95% by weight of the two-phase gel composition.

12. The two-phase gel composition of claim 1, wherein the gelled ester composition is present in the amount of about 10% to about 40% by weight of the two-phase gel composition.

13. The two-phase gel composition of claim 1, wherein the solvent is present in the amount of about 5% to about 95% by weight of the two-phase gel composition.

14. The two-phase gel composition of claim 1, wherein the solvent is present in the amount of about 60% to about 90% by weight of the two-phase gel composition.

15. The two-phase gel composition of claim 1, further comprising a suspended component.

16. The two-phase gel composition of claim 15, wherein the suspended component is a solid selected from the group consisting of organic materials, inorganic materials, organometallic materials, phosphorescent materials, and fluorescent materials.

17. The two-phase gel composition of claim 15, wherein the suspended component is a solid selected from the group consisting of zinc oxide, coated zinc oxide, surface-treated zinc oxide, titanium dioxide, coated titanium dioxide, surface-treated titanium dioxide, graphite, explosive materials, air-sensitive chemicals, moisture-sensitive chemicals, boron nitride, iron oxides, talc, mica, plastics, polymers, silica, silicon dioxide, aluminum oxide, metal particles, antibacterials, antibiotics, anesthetics, glass, clays, gums, capsules containing an active ingredient, starch, modified starch, fragrances, color pigments, sunscreen active particles, glitters, molybdenum oxide, zinc sulfide, copper-doped zinc sulfide, pesticides, herbicides, fungicides, insecticides, plasticizers, medical materials, antimicrobials, antifungals, other encapsulated materials, and combinations thereof.

18. The two-phase gel composition of claim 15, wherein the suspended component is a liquid selected from the group consisting of water, water containing a water-soluble material, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and combinations thereof.

19. The two-phase gel composition of claim 15, wherein the suspended component is a gas selected from the group consisting of hydrogen, chloride, air, nitrogen, oxygen, carbon dioxide, propane, neon, helium, and combinations thereof.

20. The two-phase gel composition of claim 1, further comprising an active ingredient.

21. The two-phase gel composition of claim 20, wherein the active ingredient is selected from the group consisting of sunscreens, antiperspirants, deodorants, perfumes, cosmetics, emollients, insect repellants, pesticides, herbicides, fungicides, plasticizers, insecticides, and medicaments.

22. A two-phase gel composition, comprising:
a gelled composition selected from the group consisting of a gelled ether composition, a gelled alcohol composition, a gelled naturally-occurring fats and oil composition, and a combination thereof, said gelled composition comprising a mixture of an ether compound, an alcohol compound, or a gelled naturally-occurring fats and oil composition and a polymer compound selected from the group consisting of diblock copolymers, triblock copolymers, star polymers, radial polymers, multi-block copolymers, and a combination thereof, the gelled composition having a viscosity $\eta_1$; and
a hydrophobic, non polar solvent, the solvent having a viscosity $\eta_2$, wherein the two-phase gel composition has a viscosity $\eta$ which is greater than or equal to $\eta_1$ and which is greater than or equal to $\eta_2$.

23. The two-phase gel composition of claim 22, wherein the two-phase gel composition has a viscosity which is substantially greater than or equal to the sum of $\eta_1$ and $\eta_2$.

24. The two-phase gel composition of claim 22, wherein the alcohols include octyl dodecanol or isostearyl alcohol.

25. The two-phase gel composition of claim 22, wherein the ethers include dicaprylyl ether or octyl methoxycinnamate.

26. The two-phase gel composition of claim 22, wherein the naturally-occurring fats and oils include linseed oil, soybean oil, sunflower seed oil, corn oil, sesame oil, olive oil, castor oil, coconut oil, palm oil, peanut oil, jojoba oil, or macadamia nut oil.

27. The two-phase gel composition of claim 22, wherein the solvent is selected from the group consisting of oils, mineral white oils, base oils, technical mineral oils, synthetic hydrocarbons, solid hydrocarbons, semi-solid hydrocarbons, waxes, petroleum distillates, petrolatums, and combinations thereof.

28. The two-phase gel composition of claim 22, wherein the gelled composition is present in the amount of about 5% to about 95% by weight of the two-phase gel composition.

29. The two-phase gel composition of claim 22, wherein the gelled composition is present in the amount of about 10% to about 40% by weight of the two-phase gel composition.

30. The two-phase gel composition of claim 22, wherein the solvent is present in the amount of about 5% to about 95% by weight of the two-phase gel composition.

31. The two-phase gel composition of claim 22, wherein the solvent is present in the amount of about 60% to about 90% by weight of the two-phase gel composition.

32. The two-phase gel composition of claim 22, further comprising a suspended component.

33. The two-phase gel composition of claim 32, wherein the suspended component is a solid selected from the group consisting of organic materials, inorganic materials, organometallic materials, phosphorescent materials, and fluorescent materials.

34. The two-phase gel composition of claim 32, wherein the suspended component is a solid selected from the group consisting of zinc oxide, coated zinc oxide, surface-treated zinc oxide, titanium dioxide, coated titanium dioxide, surface-treated titanium dioxide, graphite, explosive materials, air-sensitive chemicals, moisture-sensitive chemicals, boron nitride, iron oxides, talc, mica, plastics, polymers, silica, silicon dioxide, aluminum oxide, metal particles, antibacterials, antibiotics, anesthetics, glass, clays, gums, capsules containing an active ingredient, starch, modified starch, fragrances, color pigments, sunscreen active particles, glitters, molybdenum oxide, zinc sulfide, copper-doped zinc sulfide, pesticides, herbicides, fungicides, insecticides, plasticizers; medical materials, antimicrobials, antifungals, other encapsulated materials, and combinations thereof.

35. The two-phase gel composition of claim 32, wherein the suspended component is a liquid selected from the group consisting of water, water containing a water-soluble material, glycerin, propylene glycol, butylene glycol, alcohols, acids, surfactants, emulsifiers, polyglycerols, ethers, polar esters, fluorinated compounds, perfluoropolyethers, silicones, silicon-containing compounds, and combinations thereof.

36. The two-phase gel composition of claim 32, wherein the suspended component is a gas selected from the group consisting of hydrogen, chloride, air, nitrogen, oxygen, carbon dioxide, propane, neon, helium, and combinations thereof.

37. The two-phase gel composition of claim 22, further comprising an active ingredient.

38. The two-phase gel composition of claim 37, wherein the active ingredient is selected from the group consisting of sunscreens, antiperspirants, deodorants, perfumes, cosmetics, emollients, insect repellants, pesticides, herbicides, fungicides, plasticizers, insecticides, and medicaments.

39. A method of increasing the viscosity of a gelled composition comprising: mixing a gelled composition selected from the group consisting of a gelled ester composition, a gelled ether composition, a gelled alcohol composition, a gelled naturally-occurring fats and oil composition, and a combination thereof with a hydrophobic, non-polar solvent to form a mixture; heating the mixture; agitating the mixture until the mixture becomes homogeneous; and cooling the mixture to form a two-phase gel composition, wherein the two-phase gel composition has a viscosity which is greater than or equal to the viscosity of the gelled composition and which is greater than or equal to the viscosity of the solvent.

40. A method of increasing the viscosity of a gelled composition comprising: heating a gelled composition selected from the group consisting of a gelled ester composition, a gelled ether composition, a gelled alcohol composition, a gelled naturally-occurring fats and oil composition, and a combination thereof, mixing the heated gelled composition with a hydrophobic, non-polar solvent to form a mixture; agitating the mixture until the mixture becomes homogeneous; and cooling the mixture to form a two-phase gel composition, wherein the two-phase gel composition has a viscosity which is greater than or equal to the viscosity of the gelled composition and which is greater than or equal to the viscosity of the solvent.

41. A method of increasing the viscosity of a gelled composition comprising: heating a hydrophobic, non-polar solvent; mixing the heated solvent with a gelled composition selected from the group consisting of a gelled ester composition, a gelled ether composition, a gelled alcohol composition, a gelled naturally-occurring fats and oil composition, and a combination thereof to form a mixture; agitating the mixture until the mixture becomes homogeneous; and cooling the mixture to form a two-phase gel composition, wherein the two-phase gel composition has a viscosity which is greater than or equal to the viscosity of the gelled composition and which is greater than or equal to the viscosity of the solvent.

42. A method of increasing the viscosity of a gelled composition comprising: heating a hydrophobic, non-polar solvent; separately heating a gelled composition selected from the group consisting of a gelled ester composition, a gelled ether composition, a gelled alcohol composition, a gelled naturally-occurring fats and oil composition, and a combination thereof; mixing the heated solvent with the heated gelled composition to form a mixture; agitating the mixture until the mixture becomes homogeneous; and cooling the mixture to form a two-phase gel composition, wherein the two-phase gel composition has a viscosity which is greater than or equal to the viscosity of the gelled composition and which is greater than or equal to the viscosity of the solvent.

43. A method of increasing the viscosity of a gelled composition comprising: mixing a gelled composition selected from the group consisting of a gelled ester composition, a gelled ether composition, a gelled alcohol composition, a gelled naturally-occurring fats and oil composition, and a combination thereof with a hydrophobic, non-polar solvent to form a two-phase gel composition, wherein the two-phase gel composition has a viscosity which is greater than or equal to the viscosity of the gelled composition and which is greater than or equal to the viscosity of the solvent.

44. The method of claim 43, wherein the two-phase gel composition has a viscosity which is substantially greater than or equal to the viscosity of the gelled composition and which is substantially greater than or equal to the viscosity of the solvent.

45. The method of claim 43, wherein the two-phase gel composition has a viscosity which is substantially greater than or equal to the sum of the viscosity of the gelled composition and the viscosity of the solvent.

46. The method of claim 43, wherein the gelled ester composition comprises a mixture of an ester compound and a polymer compound selected from the group consisting of triblock copolymers, star polymers, radial polymers, multi-block copolymers, and a combination thereof.

47. The method of claim 43, wherein the gelled ether composition comprises a mixture of an ether compound and a polymer compound selected from the group consisting of diblock copolymers, triblock copolymers, star polymers, radial polymers, multi-block copolymers, and a combination thereof.

48. The method of claim 43, wherein the gelled alcohol composition comprises a mixture of an alcohol compound and a polymer compound selected from the group consisting of diblock copolymers, triblock copolymers, star polymers, radial polymers, multi-block copolymers, and a combination thereof.

49. The method of claim 43, wherein the gelled naturally-occurring fats and oil composition comprises a mixture of a naturally-occurring fats and oil compound and a polymer compound selected from the group consisting of diblock copolymers, triblock copolymers, star polymers, radial polymers, multi-block copolymers, and a combination thereof.

* * * * *